United States Patent [19]

Harris et al.

[11] 4,374,829

[45] Feb. 22, 1983

[54] AMINOACID DERIVATIVES AS ANTIHYPERTENSIVES

[75] Inventors: Elbert E. Harris; Arthur A. Patchett, both of Westfield; Edward W. Tristram, Watchung; Matthew J. Wyvratt, Mountainside, all of N.J.

[73] Assignee: Merck & Co., Inc., Rahway, N.J.

[21] Appl. No.: 235,335

[22] Filed: Feb. 17, 1981

Related U.S. Application Data

[63] Continuation-in-part of Ser. No. 79,898, Oct. 9, 1979, abandoned, which is a continuation-in-part of Ser. No. 36,279, May 7, 1979, abandoned, which is a continuation-in-part of Ser. No. 968,249, Dec. 11, 1978, abandoned.

[51] Int. Cl.$^3$ .................... A61K 37/00; C07C 103/52; C07D 207/24
[52] U.S. Cl. .............................. 424/177; 260/112.5 R
[58] Field of Search ...................... 260/326.2, 112.5 R; 424/177

[56] References Cited

PUBLICATIONS

Theohanson, et al., J. Biol. Chem. 175, (1948) 833–848.

*Primary Examiner*—Delbert R. Phillips
*Attorney, Agent, or Firm*—Salvatore C. Mitri; Martin L. Katz

[57] ABSTRACT

The invention relates to new carboxyalkyl dipeptide derivatives and related compounds which are useful as antihypertensives.

82 Claims, No Drawings

AMINOACID DERIVATIVES AS ANTIHYPERTENSIVES

RELATED APPLICATIONS

This application is a continuation-in-part of U.S. Ser. No. 079,898 filed Oct. 9, 1979 which is a continuation-in-part of U.S. Ser. No. 036,279 filed May 7, 1979, both now abandoned, which is a continuation-in-part of U.S. Ser. No. 968,249 filed Dec. 11, 1978, now abandoned.

BACKGROUND OF THE INVENTION

U.S. Pat. Nos. 4,129,571 and 4,154,960 disclose substituted acyl derivatives of amino acids which are useful as angiotension converting enzyme inhibitors. More specifically, these compounds are mercapto substituted acyl amino acids and derivatives thereof including the clinically effective antihypertensive compound, captopril, i.e., D-3-mercapto-2-methylpropanoyl-L-proline.

The foregoing prior art compounds are not dipeptide derivatives as are the compounds of the present invention. Furthermore, these prior art compounds contain an essential sulfhydryl substituent or derivative thereof whereas those of the present invention do not. In addition, the dipeptide compounds of the present invention are unusual dipeptides whose N-terminus bears a carboxymethyl group which is preferably further substituted on the methyl group. In addition, the carboxyl group(s) may also be converted to ester, amide and salt derivatives. In effect, the compounds of the present invention are hybrids formed by fusing α-amino acids onto dipeptides by means of a nitrogen shared by these two part-structures. This structural arrangement is rare in the field of synthetic and natural peptides and is not suggested or disclosed by the mercaptoacyl type functions of the two prior art patents identified above.

U.S. Pat. No. 4,052,511 discloses N-carboxyalkanoylamino acids which are useful as angiotension converting enzyme inhibitors. Since the compounds of the present invention are dipeptide derivatives, in a formal sense they may be considered to be related to some of the compounds disclosed in U.S. Pat. No. 4,052,511. However, when a particular one of the methylene groups is replaced by an amino function as in the present invention, compounds of surprisingly high potency are obtained. For example, the preferred compounds of the present invention can be administered in dosages as low as about 2.5 mg. per patient per day as opposed to the lowest dosage level of 1 mg. per kg. per day for preferred compounds disclosed in the U.S. Pat. No. 4,052,511 patent whch is about equivalent to 60 mg. per patient per day based on an average patient weight of about 150 pounds.

SUMMARY OF THE INVENTION

The invention in its broad aspects relates to carboxyalkyl dipeptides and derivatives thereof which are useful as converting enzyme inhibitors and as antihypertensives. The compounds of this invention can be shown by the following formula:

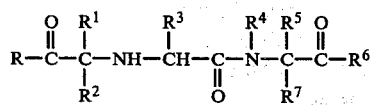

wherein

R and $R^6$ are the same or different and are hydroxy,
  lower alkoxy,
  lower alkenoxy,
  dilower alkylamino lower alkoxy (dimethylaminoethoxy),
  acylamino lower alkoxy (acetylaminoethoxy),
  acyloxy lower alkoxy (pivaloyloxymethoxy),
  aryloxy, such as phenoxy,
  arloweralkoxy, such as benzyloxy,
  substituted aryloxy or substituted arloweralkoxy wherein the substitutent is methyl, halo or methoxy,
  amino,
  loweralkylamino,
  diloweralkylamino,
  hydroxyamino,
  arloweralkylamino such as benzylamino;
$R^1$ is hydrogen,
  alkyl of from 1 to 20 carbon atoms which include branched and cyclic and unsaturated (such as allyl) alkyl groups,
  substituted loweralkyl wherein the substituent can be halo, hydroxy, lower alkoxy, aryloxy such as phenoxy, amino, diloweralkylamino, acylamino, such as acetamido and benzamido, arylamino, guanidino, imidazolyl, indolyl, mercapto, loweralkylthio, arylthio such as phenlthio, carboxy or carboxamido, carboloweralkoxy,
  aryl such as phenyl or naphthyl,
  substituted aryl such as phenyl wherein the substituent is lower alkyl, lower alkoxy or halo,
  arloweralkyl, arloweralkenyl, heteroarlower alkyl or heteroarlower alkenyl such as benzyl, styryl or indolyl ethyl,
  substituted arloweralkyl, substituted arloweralkenyl, substituted heteroarlower alkyl, or substituted heteroarlower alkenyl, wherein the substituent(s) is halo, dihalo, lower alkyl, hydroxy, lower alkoxy, amino, aminomethyl, acylamino (acetylamino or benzoylamino) diloweralkylamino, loweralkylamino, carboxyl, haloloweralkyl, cyano or sulfonamido;
  ar'oweralkyl or heteroarloweralkyl substituted on the alkyl portion by amino or acylamino (acetylamino or benzoylamino);
$R^2$ and $R^7$ are the same or different and are hydrogen or lower alkyl;
$R^3$ is hydrogen, lower alkyl, phenyl lower alkyl, aminomethyl phenyl lower alkyl, hydroxy phenyl lower alkyl, hydroxy lower alkyl, acylamino lower alkyl (such as benzoylamino lower alkyl, acetylamino lower alkyl), amino lower alkyl, dimethylamino lower alkyl, halo lower alkyl, guanidino lower alkyl, imidazolyl lower alkyl, indolyl lower alkyl, mercapto lower alkyl, lower alkyl thio lower alkyl;
$R^4$ is hydrogen or lower alkyl;
$R^5$ is hydrogen, lower alkyl, phenyl, phenyl lower alkyl, hydroxy phenyl lower alkyl, hydroxy lower alkyl, amino lower alkyl, guanidino lower alkyl, imidazolyl lower alkyl, indolyl lower alkyl, mercapto lower alkyl or lower alkyl thio lower alkyl;
$R^4$ and $R^5$ may be connected together to form an alkylene bridge of from 2 to 4 carbon atoms, an alkylene bridge of from 2 to 3 carbon atoms and one sulfur atom, an alkylene bridge of from 3 to 4 carbon atoms containing a double bond or an alkylene bridge as above substituted with hydroxy, loweralkoxy, loweralkyl or diloweralkyl;

and the pharmaceutically acceptable salts thereof.

The loweralkyl or lower alkenyl groups except where noted otherwise represented by any of the variables include straight and branched chain hydrocarbon radicals from one to six carbon atoms, for example, methyl, ethyl, propyl, isopropyl, butyl, isobutyl, t-butyl, pentyl, isopentyl, hexyl or vinyl, allyl, butenyl and the like. The aralkyl groups represented by any of the above variables have from one to four carbon atoms in the alkyl portion thereof and include for example, benzyl, p-methoxy benzyl and the like. Halo means chloro, bromo, iodo or fluoro. Aryl where it appears in any of the radicals except where noted represents phenyl or naphthyl. Heteroaryl groups where they appear include for example pyridyl, thienyl, furyl, indolyl, benzthienyl, imidazoyl and thiazolyl.

The $R^1$, $R^3$ and $R^5$ substituted lower alkyl moieties are exemplified by groups such as

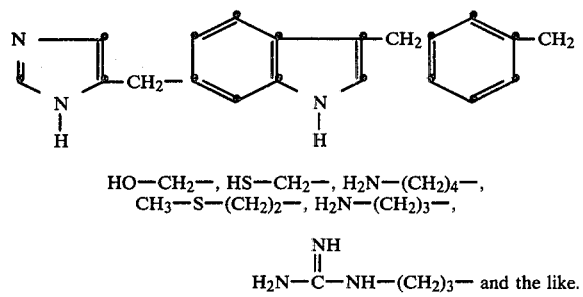

$HO-CH_2-$, $HS-CH_2-$, $H_2N-(CH_2)_4-$,
$CH_3-S-(CH_2)_2-$, $H_2N-(CH_2)_3-$,

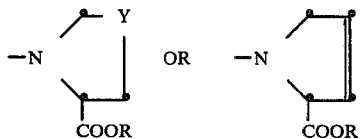 and the like.

$R^4$ and $R^5$ when joined through the carbon and nitrogen atoms to which they are attached form a 4 to 6 membered ring which may contain one sulfur atom or a double bond. Preferred rings have the formulae:

$$-N\diagup\diagdown_{COOR}^{Y} \quad OR \quad -N\diagup\diagdown_{COOR}$$

where Y is $CH_2$, S, or $CHOCH_3$.

Preferred are those compounds of Formula I wherein:

R and $R^6$ can each independently by hydroxy, lower alkoxy, lower alkenoxy, arloweralkyloxy, amino, dilower alkylamino lower alkoxy, acylamino lower alkoxy, acyloxy lower alkoxy wherein the substituent is methyl, halo or methoxy;

$R^2$ and $R^7$ are hydrogen;

$R^3$ is lower alkyl, amino lower alkyl, imidazoyl lower alkyl, halo lower alkyl;

$R^4$ and $R^5$ are joined to form the preferred rings as defined above where Y is $CH_2$, S, or $CH-OCH_3$;

$R^1$ is as defined previously.

Still more preferred compounds are those preferred compounds of Formula I wherein further $R^1$ is alkyl having from 1 to 8 carbon atoms, substituted lower alkyl wherein the alkyl group has 1-5 carbon atoms and the substituent is amino, arylthio, aryloxy or arylamino, aralkyl or heteroaralkyl wherein the alkyl portion has 1 to 3 carbon atoms such as phenethyl or indolylethyl or substituted arloweralkyl (phenyl lower alkyl or naphthyl lower alkyl) and substituted heteroarloweralkyl wherein the alkyl groups have 1-3 carbons and wherein the substituent(s) is halo, dihalo, amino, aminoalkyl, hydroxy, lower alkoxy or lower alkyl. Most preferred are compounds of Formula I wherein R and $R^6$ are hydroxy, lower alkoxy, aralkyloxy;

$R^2$ and $R^7$ are hydrogen;

$R^3$ is methyl or amino lower alkyl;

$R^4$ and $R^5$ are joined through the carbon and nitrogen atom to form proline, 4-thiaproline or 4-methoxy proline;

$R^1$ is alkyl having from 1 to 8 carbon atoms, substituted lower alkyl wherein the alkyl group has 1-5 carbon atoms and the substituent is amino, arylthio or aryloxy, aralkyl or heteroaralkyl wherein the alkyl portion has 1 to 3 carbon atoms such as phenethyl or indolylethyl or substituted aralkyl (phenyl lower alkyl or naphthyl lower alkyl) and substituted heteroaralkyl wherein the alkyl groups have 1-3 carbons and wherein the substituent(s) is halo, dihalo, amino, aminoalkyl, hydroxy, lower alkoxy or lower alkyl.

The preferred, more preferred and most preferred compounds also include the pharmaceutically acceptable salts thereof and are exemplified by such compounds as:

N-(1(S)-carboxy-3-phenylpropyl)-L-alanyl-L-proline;

N-(1(S)-ethoxycarbonyl-3-phenylpropyl)-L-alanyl-L-proline and its maleate salt;

N-(1(S)-ethoxycarbonyl-4-methylpentyl)-L-alanyl-L-proline;

N-(1-carboxy-5-aminopentyl)-L-alanyl-L-proline;

N-α-(1(S)-carboxy-3-phenylpropyl)-L-lysyl-L-proline;

N-α(1(S)-ethoxycarbonyl-3-phenylpropyl)-L-lysyl-L-proline;

N-α[1(S)-carboxy-3-(3-indolyl)propyl]-L-lysyl-L-proline;

N-α-[1(S)-carboxy-3-(4-chlorophenyl)-propyl]-L-lysyl-L-proline;

N-α-[1(S)-carboxy-2-phenylthioethyl]-L-lysyl-L-proline;

N-α-[1(S)-carboxy-3-(4-chlorophenyl)-propyl]-L-lysyl-L-4α-methoxyproline;

N-α-[1(S)-carboxy-5-aminopentyl]-L-lysyl-L-proline;

Ethyl N-(1(S)-ethoxycarbonyl-3-phenylpropyl)-L-alanyl-L-prolinate hydrochloride;

and the like.

The products of Formula (I) and the preferred subgroups can be produced by one or more of the methods and subroutes depicted in the following equations:

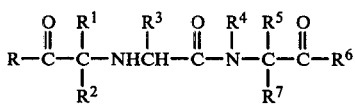

As will be evident to those skilled in the art and as demonstrated in the Examples, reactive groups not involved in the condensations, such as amino, carboxy, mercapto, etc., may be protected by methods standard in peptide chemistry prior to the coupling reactions and subsequently deprotected to obtain the desired products.

Method I, Route 1 ($R^2=H$)

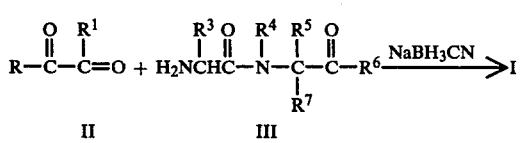

Keto acid (or ester, amide or hydroxamic acid) II is condensed with dipeptide III in aqueous solution, optimally near neutrality, or in suitable organic solvent ($CH_3CN$ for example) in the presence of sodium cyano borohydride to give I ($R^2=H$). Alternatively the intermediate Schiff base, enamine, or aminol may be catalytically reduced to yield product I, for example, by hydrogen in the presence of 10% palladium on carbon or of Raney nickel. The ratio of diasteriomeric products formed may be altered by choice of catalyst.

If R and $R^6$ are carboxy protecting groups such as alkoxy or benzyloxy or the like, they can be converted by well-known methods such as hydrolysis or hydrogenation to (I), where R and/or $R^6$ are hydroxy. This is true in all the following methods where the above situation exists.

Alternatively II can be condensed with an amino acid IV

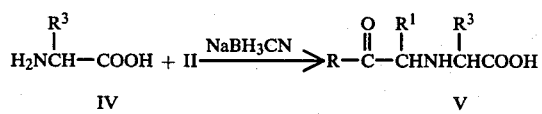

under the same conditions to yield amino acid V. Subsequent coupling by known methods with amino acid derivative VI gives I.

The known methods encompass reactive group protection during the coupling reaction, for example, by N-formyl, N-t-butoxycarbonyl and N-carbobenzyloxy groups followed by their removal to yield I. Furthermore, the R function may include removable ester groups such as benzyl, ethyl, or t-butyl. Condensing agents in this synthetic route are typically those useful in peptide chemistry such as dicyclohexylcarbodiimide (DCC) or diphenylphosphoryl azide (DPPA) or V may be activated via the intermediacy of active esters such as that derived from 1-hydroxybenzotriazole.

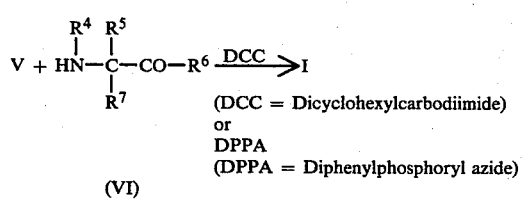

Route 2

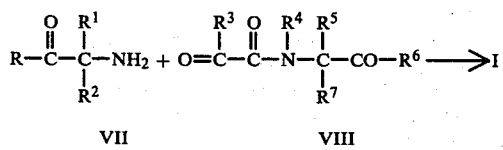

Amino acid (or ester, amide or hydroxamic acid) VII is condensed with ketone VIII under conditions described for Route I to give I.

Alternatively the synthesis can be performed in a step-wise fashion by condensing VII with keto acid IX.

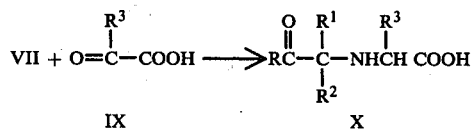

to yield amino acid X. By known methods as indicated above under Route 1, X can be condensed with amino acid derivative VI to give I.

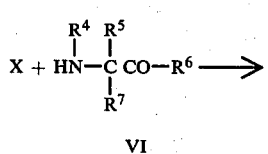

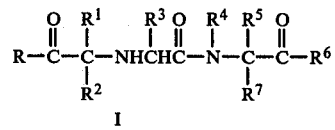

In the special case of $R^1$ bearing an α-amino substituent, the carbonyl and amino groups can be conveniently protected as a β-lactam function.

Method 2 Route 1

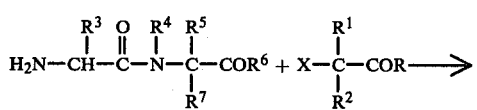

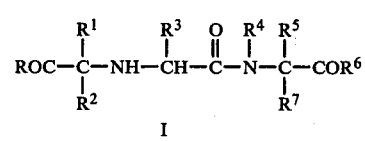

The dipeptide III is alkylated with the appropriate α-haloacid (ester or amide) or α-sulfonyloxy acid (ester or amide) XI under basic conditions in water or an organic solvent.

X is chlorine, bromine, iodine or alkyl sulfonyloxy or aryl sulfonyloxy.

Alternatively the synthesis can be performed in a stepwise fashion.

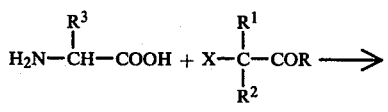

-continued

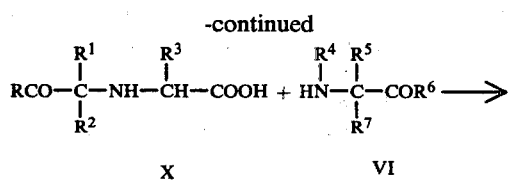

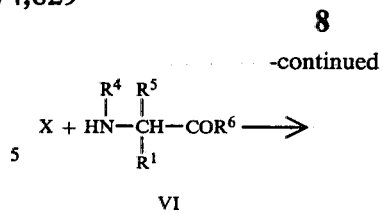

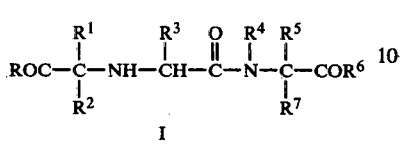

X

VI

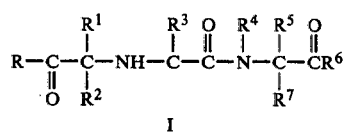

VI

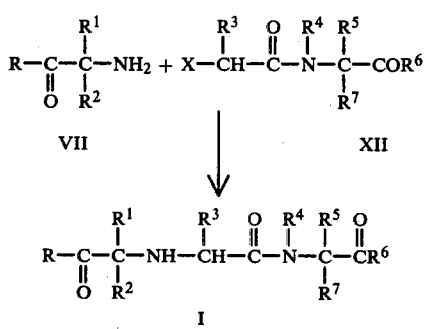

I

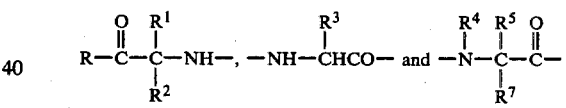

I

X=Cl, Br, I, alkylsulfonyloxy or arylsulfonyloxy.

The aminoacid IV is alkylated by the α-haloacid (ester or amide) or α-sulfonyloxy acid (ester or amide) XI under basic conditions to yield compounds X. This is condensed by standard methods as indicated under Route 1 with the aminoacid (ester or amide) VI to afford I.

Reductive cleavage of a benzyl ester I (where $R^6$ is benzyloxy and R is alkoxy) will yield compounds of Formula I wherein R is alkoxy and $R^6$ is hydroxy, and where $R^6$ is alkoxy and R is benzyloxy, will yield compounds of Formula I wherein R is hydroxy and $R^6$ is alkoxy.

Route 2

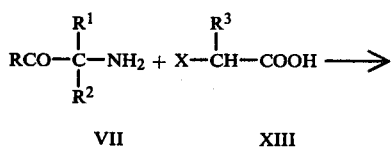

VII    XIII

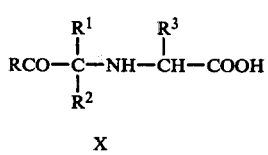

X

α-haloacetic acid or α-sulfonyloxy acetic acid (XIII) to yield the intermediate X. By known methods described under Route 1, X can be coupled with an aminoacid VI or derivative to give I. In the above methods, an aralkyloxy moiety can be employed for either or both R and $R^6$ to provide an ester or diester.

As desired, protecting groups may be removed by known methods.

The starting materials which are required for the above processes herein described are known in the literature or can be made by known methods from known starting materials.

In products of general Formula I, the carbon atoms to which $R^1$, $R^3$ and $R^5$ are attached may be asymmetric. The compounds accordingly exist in disastereoisomeric forms or in mixtures thereof. The above described syntheses can utilize racemates, enantiomers or diastereomers as starting materials. When diastereomeric products result from the synthetic procedures, the diastereomeric products can be separated by conventional chromatographic or fractional crystallization methods. Although, the aminoacid part-structures, i.e., $$R-\overset{O}{\overset{\|}{C}}-\overset{R^1}{\underset{R^2}{\overset{|}{C}}}-NH-, \quad -NH-CHCO-\underset{R^3}{} \quad \text{and} \quad -\overset{R^4}{\underset{}{\overset{|}{N}}}-\overset{R^5}{\underset{R^7}{\overset{|}{C}}}-\overset{O}{\overset{\|}{C}}-$$

of Formula (I) are generally preferred in the L- or S-configuration, diastereomers containing D-amino acids have activity dependent upon their structures and have advantages in respect to metabolic stability in vivo and therefore can be utilized in mixture or as pure diastereomeric compounds.

The compounds of this invention form salts with various inorganic and organic acids and bases which are also within the scope of the invention. Such salts include ammonium salts, alkali metal salts like sodium and potassium salts, alkaline earth metal salts like the calcium and magnesium salts, salts with organic bases e.g., dicyclohexylamine salts, N-methyl-D-glucamine, salts with amino acids like arginine, lysine and the like. Also salts with organic and inorganic acids may be prepared, e.g., HCl, HBr, $H_2SO_4$, $H_3PO_4$, methane-sulfonic, toluensulfonic, maleic, fumaric, camphorsulfonic. The nontoxic physiologically acceptable salts are preferred, although other salts are also useful, e.g., in isolating or purifying the product.

The salts may be formed by conventional means, as by reacting the free acid or free base forms of the product with one or more equivalents of the appropriate base or acid in a solvent or medium in which the salt is insoluble, or in a solvent such as water which is then removed in vacuo or by freeze-drying or by exchanging X=Cl, Br, I, alkyl sulfonyloxy or aryl sulfonyloxy.

The aminoacid or derivative VII is alkylated with the appropriately substituted α-haloacetyl or α-sulfonyloxy acetyl aminoacid XII (preferably with $R^6$ not hydroxyl) under basic conditions in water or other solvent to obtain compounds of Formula I.

Alternatively, the synthesis can be performed in a step-wise fashion by condensing an aminoacid ester VII with a substituted the cations of an existing salt for another cation on a suitable ion exchange resin.

The compounds of this invention inhibit angiotensin converting enzyme and thus block conversion of the decapeptide angiotensin I to angiotensin II. Angiotensin II is a potent pressor substance. Thus blood-pressure lowering can result from inhibition of its biosynthesis especially in animals and humans whose hypertension is angiotensin II related. Furthermore, converting enzyme degrades the vasodepressor substance, bradykinin. Therefore, inhibitors of angiotensin converting enzyme may lower blood-pressure also by potentiation of bradykinin. Although the relative importance of these and other possible mechanisms remains to be established, inhibitors of angiotensin converting enzyme are effective antihypertensive agents in a variety of animal models and are useful clinically, for example, in many human patients with renovascular, malignant and essential hypertension. See, for example, D. W. Cushman et al., *Biochemistry* 16, 5484 (1977).

The evaluation of converting enzyme inhibitors is guided by in vitro enzyme inhibition assays. For example, a useful method is that of Y. Piquilloud, A. Reinharz and M. Roth, *Biochem. Biophys. Acta*, 206, 136 (1970) in which the hydrolysis of carbobenzyloxyphenylalanylhistidinylleucine is measured. In vivo evaluations may be made, for example, in normotensive rats challenged with angiotensin I by the technique of J. R. Weeks and J. A. Jones, *Proc. Soc. Exp. Biol. Med.*, 104, 646 (1960) or in a high renin rat model such as that of S. Koletsky et al., *Proc. Soc. Exp. Biol. Med.*, 125, 96 (1967).

Thus, the compounds of the invention are useful in treating hypertension. They are also of value in the management of acute and chronic congestive heart failure, in the treatment of secondary hyperaldosteronism, primary and secondary pulmonary hypertension, renal failure and renal vascular hypertension, and in the management of vascular disorders such as migraine or Raynaud's disease. The application of the compounds of this invention for these and similar disorders will be apparent to those skilled in the art.

In the management of hypertension and those clinical conditions noted above, the compounds of this invention may be utilized in compositions such as tablets, capsules or elixirs for oral administration, suppositories for rectal administration, sterile solutions or suspensions for parenteral or intramuscular administration, and the like. The compounds of this invention can be administered to patients (animals and human) in need of such treatment in dosages that will provide optimal pharmaceutical efficacy. Although the dose will vary from patient to patient depending upon the nature and severity of disease, the patient's weight, special diets then being followed by a patient, concurrent medication, and other factors which those skilled in the art will recognize, the dosage range will generally be about 1 to 1000 mg. per patient per day which can be administered in single or multiple doses. Preferably, the dosage range will be about 2.5 to 250 mg. per patient per day; more preferably about 2.5 to 75 mg. per patient per day.

The compounds of this invention can also be administered in combination with other antihypertensives and/or diuretics. For example, the compounds of this invention can be given in combination with such compounds as amiloride, atenolol, bendroflumethiazide, chlorothalidone, chlorothiazide, clonidine, cryptenamine acetates and cryptenamine tannates, deserpidine, diazoxide, guanethidene sulfate, hydralazine hydrochloride, hydrochlorothiazide, hydroflumethiazide, metolazone, metoprololtartate, methyclothiazide, methyldopa, methyldopate hydrochloride, minoxidil, pargyline hydrochloride, polythiazide, prazosin, propranolol, *rauwolfia serpentina*, rescinnamine, reserpine, sodium nitroprusside, spironolactone, timolol, trichlormethiazide, trimethophan camsylate, benzthiazide, quinethazone, ticrynafan, triamterene, acetazolamide, aminophylline, cyclothiazide, ethacrynic acid, furosemide, merethoxylline procaine, sodium ethacrynate, and the like, as well as admixtures and combinations thereof.

Typically, the individual daily dosages for these combinations can range from about one-fifth of the minimally recommended clinical dosages to the maximum recommended levels for the entities when they are given singly.

To illustrate these combinations, one of the antihypertensives of this invention effective clinically in the 2.5–250 milligrams per day range can be effectively combined at levels at the 0.5–250 milligrams per day range with the following compounds at the indicated per day dose range: hydrochlorothiazide (15–200 mg), chlorothiazide (125–2000 mg), ethacrynic acid (15–200 mg), amiloride (5–20 mg), furosemide (5–80 mg), propranolol (20–480 mg), timolol (5–60 mg.) and methyldopa (65–2000 mg). In addition, triple drug combinations of hydrochlorothiazide (15–200 mg) plus amiloride (5–20 mg) plus converting enzyme inhibitor of this invention (3–200 mg) or hydrochlorothiazide (15–200 mg) plus timolol (5–60) plus the converting enzyme inhibitor of this invention (0.5–250 mg) are effective combinations to control blood pressure in hypertensive patients. Naturally, these dose ranges can be adjusted on a unit basis as necessary to permit divided daily dosage and, as noted above, the dose will vary depending on the nature and severity of the disease, weight of patient, special diets and other factors.

Typically, these combinations can be formulated into pharmaceutical compositions as discussed below.

About 1 to 100 mg. of a compound or mixture of compounds of Formula I or a physiologically acceptable salt is compounded with a physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

Illustrative of the adjuvants which may be incorporated in tablets, capsules and the like are the following: a binder such as gum tragacanth, acacia, corn starch or gelatin; an excipient such as microcrystalline cellulose; a disintegrating agent such as corn starch, pregelatinized starch, alginic acid and the like; a lubricant such as magnesium stearate; a sweetening agent such as sucrose, lactose or saccharin; a flavoring agent such as peppermint, oil of wintergreen or cherry. When the dosage unit form is a capsule, it may contain in addition to materials of the above type, a liquid carrier such as fatty oil. Various other materials may be present as coatings or to otherwise modify the physical form of the dosage unit. For instance, tablets may be coated with shellac, sugar or both. A syrup or elixir may contain the active compound, sucrose as a sweetening agent, methyl and propyl parabens as preservatives, a dye and a flavoring such as cherry or orange flavor.

Sterile compositions for injection can be formulated according to conventional pharmaceutical practice by dissolving or suspending the active substance in a vehicle such as water for injection, a naturally occurring vegetable oil like sesame oil, coconut oil, peanut oil, cottonseed oil, etc. or a synthetic fatty vehicle like ethyl oleate or the like. Buffers, preservatives, antioxidants and the like can be incorporated as required.

The following examples are illustrative of the invention and constitute especially preferred embodiments. The preferred diastereomers of these examples are isolated by column chromatography or fractional crystallization.

EXAMPLE 1

N-(1-Carboxy-2-phenylethyl)-L-alanyl-L-proline

A mixture of phenylpyruvic acid (753 mg) and L-alanyl-L-proline (171 mg) in methanol-water are adjusted to pH 6.8 and treated with sodium cyanoborohydride (173 mg) at room temperature until reaction is complete. The product is absorbed on strong cation exchange resin and eluted with 2% pyridine in water to give 294 mg of crude diastereomeric product, N-(1-carboxy-2-phenylethyl)-L-alanyl-L-proline. A portion is purified by gel filtration (LH-20) for spectrographic analysis. The nmr spectrum shows a broad singlet at 7.2, complex absorption from 3.0 to 4.6, a multiplet at 2.1 and a pair of doublets at 1.5 ppm.

EXAMPLE 2

N-(1-Carboxyethyl)-L-alanyl-L-proline

A solution of L-alanyl-L-proline (372 mg) and pyruvic acid (881 mg) in water is adjusted to pH 7 and treated with 377 mg of sodium cyanoborohydride at room temperature until reaction is complete. The product is absorbed on strong acid ion-exchange resin and then eluted with 2% pyridine in water. Freeze drying gives 472 mg of N-(1-carboxyethyl)-L-alanyl-L-proline. Nmr and mass spectrogram are consistent with structure. The nmr spectrum shows multiplets centered at 4.5, 3.7, and 2.2 ppm, and a pair of doublets and 1.6 ppm.

EXAMPLE 3

N-(1-Carboxy-2-cyclohexylethyl)-L-alanyl-L-proline

3-Cyclohexyl-2-oxopropionic acid (cyclohexylpyruvic acid) (0.98 g) and L-alanyl-L-proline (0.22 g) were treated with sodium cyanoborohydride (0.22 g) as described above. A light colored solid, N-(1-carboxy-2-cyclohexylethyl)-L-alanyl-L-proline, was obtained, 0.31 g. After purification by chromatography the mass spectrum showed peaks at 340 (molecular ion), 322, 277, 249, and 226. The nmr spectrum showed complex absorption in the 4.8 to 3.6 range, and peaks at 2.2, 1.7, and 1.2 ppm.

EXAMPLE 4

N-(1-Carboxy-5-methylhexyl)-L-alanyl-L-proline

6-Methyl-2-oxoheptanoic acid (0.90 g) and L-alanyl-L-proline (0.21 g) were treated with sodium cyanoborohydride (0.21 g) as described above. A white fluffy solid, N-(1-carboxy-5-methylhexyl)-L-alanyl-L-proline (0.24 g) was obtained. After purification by chromatography the mass spectrum showed a peak at 472 (disilyl derivative). The nmr spectrum showed absorption centered at 4.5, 3.65, 2.0, 1.6, 1.3, and 0.85 ppm.

EXAMPLE 5

N-(1-Carboxy-3-methylbutyl)-L-alanyl-L-proline

4-Methyl-2-oxopentanoic acid (1.29 g) and L-alanyl-L-proline (0.32 g) were treated with sodium cyanoborohydride (0.32 g) as described above. A fluffy white solid, N-(1-carboxy-3-methylbutyl)-L-alanyl-L-proline, was obtained (0.40 g). A portion was purified by chromatography. The mass spectrum showed a peak at 429 (molecular ion of disilyl derivative minus methyl, 444-15). The nmr spectrum showed resonances centered at 4.4, 3.6, 2.1, 1.6, and 0.95 ppm.

EXAMPLE 6

N-(1-Carboxypropyl)-L-alanyl-L-proline

2-Oxobutyric acid (1.02 g) and L-alanyl-L-proline (0.37 g) were treated with sodium cyanoborohydride (0.38 g) as described above. Crude N-1-carboxypropyl)-L-alanyl-L-proline (0.42 g) was obtained. A portion was chromatographed for spectral analysis. The mass spectrum showed prominent peaks at 254 (M-18) and 210 (M-62). The nmr spectrum displayed complex absorption from 4.5 to 3.4, a multiplet centered at 2.0 and methyl resonances centered at 1.55 and 0.95 ppm.

EXAMPLE 7

N-(1-carboxy-2-methylpropyl)L-alanyl-L-proline

A mixture of 3-methyl-2-oxobutyric acid sodium salt (1.46 g) and L-alanyl-L-proline (0.40 g) was treated with sodium cyanoborohydride (0.41 g) as described above. Crude N-(1-carboxy-2-methylpropyl)L-alanyl-L-proline (0.45 g) was obtained by elution from ion-exchange resin. The product melted at 131°–142°. The nmr spectrum shows complex absorption in the 4.6 to 3.3 region, a broad multiplet centered at 2.2 and doublets at 1.65 and 1.1 ppm.

EXAMPLE 8

N-(1,3-Dicarboxypropyl)-L-alanyl-L-proline

2-Oxoglutaric acid (1.46 g) and L-alanyl-L-proline (0.37 g) were treated with sodium cyanoborohydride (0.38 g) as described above. Crude N-(1,3-dicarboxypropyl)-L-alanyl-L-proline (0.47 g) was obtained, m.p. 140°–160°. The mass spectrum of silylated material showed an ion at 517 m/e equivalent to the molecular ion for the trisilylated derivative minus methyl (532-15). The nmr spectrum was consistent with structure. Methyl resonances were centered at 1.4 ppm.

EXAMPLE 9

N-(1,4-Dicarboxybutyl)-L-alanyl-L-proline

2-Oxoadipic acid (1.74 g) and L-alanyl-L-proline (0.41 g) were treated with sodium cyanoborohydride (0.42 g) as described above. Crude N-1,4-dicarboxybutyl)-L-alanyl-L-proline (0.35 g) was obtained, m.p. 106°–132°. The highest peak in the mass spectrum was 312 corresponding to the molecular ion minus water. The methyl resonances in the nmr spectrum show a pair of doublets centered at 1.55 ppm.

EXAMPLE 10

N-(1-Carboxy-3-methylbutyl)-L-alanyl-L-isoleucine

A solution of L-alanyl-L-isoleucine (150 mg) and 4-methyl-2-oxopentanoic acid sodium salt (564 mg) in water was adjusted to pH 7 and treated with 140 mg of sodium cyanoborohydride at room temperature for several days. The reaction was quenched with strong acid ion-exchange resin, added to a column of the same resin, and eluted with 2% pyridine in water. Freeze drying afforded 200 mg (84.9%) of white fluffy solid, N-(1-carboxy-3-methylbutyl)-L-alanyl-L-isoleucine.

Mass spectrum showed peaks at 460 for the disilylated derivative, and 445 for disilyl molecular ion minus methyl (460–15). The nmr spectrum showed a broad doublet centered at 0.95 ppm, complex absorption in the 1.2–1.8 ppm range, and a broad weak singlet at 3.7 ppm.

EXAMPLE 11

N-(1-Carboxy-3-methylbutyl)-L-alanyl-L-phenylalanine

A solution of L-alanyl-L-phenylalanine (150 mg) and 4-methyl-2-oxopentanoic acid sodium salt (483 mg) in water was adjusted to pH 7 and treated with 120 mg of sodium cyanoborohydride at room temperature for several days. The reaction was quenched with Dowex 50 (H+), added to a column of the same resin and eluted with 2% pyridine in water. Freeze drying yielded 197 mg (88.7%) of white fluffy solid. N-(1-carboxy-3-methylbutyl)-L-alanyl-L-phenylalanine. Mass spectrum showed peaks at 551 for the trisilyl derivative minus methyl (566–15), 479 for the disilyl derivative minus methyl (494–15), and 449 for the trisilyl derivative minus—COOTMS (566–117). The nmr spectrum showed broad doublets at 0.95 and 1.5 ppm, complex weak absorption in the 2.8—3.4 ppm range, and a singlet at 7.1 ppm. Integration was consistent with structure giving the proper ratio of aromatic to aliphatic protons.

EXAMPLE 12

N-Carboxymethyl-L-alanyl-L-proline

In a small flask fitted with a pH electrode combine 1.05 g of L-alanyl-L-proline and 1.2 ml of 4 M NaOH. Add 0.53 g of chloroacetic acid in 1.2 ml of 2 M NaOH. Adjust the pH to 8–9, heat to 85°, and hold the pH at 8–9 for 15 minutes by adding NaOH as necessary. Add another 0.53 g of chloroacetic acid and NaOH as necessary for 15 minutes. Charge a third 0.53 g portion of chloroacetic acid, hold the pH at 8–9 for 15 minutes, age an additional 15 minutes at 85° and cool.

Pass the reaction mixture over a column of Dowex 50 (H+), wash with water and elute with 2% pyridine in water. Combine the fractions which show a positive ninhydrin reaction, concentrate to a small volume in vacuo, and freeze dry.

Dissolve this material in a few ml of water and charge to a column of Dowex 50 (Na+). Elute with 0.5 M citric acid adjusted to pH 3.3 with NaOH. The desired product emerges first (ninhydrin test), well resolved from unreacted alanylproline. Concentrate the product fraction in vacuo to a weight of about 300 g.

Charge this solution to a column of Dowex 50 (H+). Wash with water, then elute the product with 2% pyridine in water. Concentrate the product fraction in vacuo to a small volume and freeze dry. Yield 417 mg of N-carboxymethyl-L-alanyl-L-proline.

nmr spectrum ($D_2O$, MeOH internal standard): 1.58 ppm (d, J=6) with small companion at 1.53 (d, J=6) (total 3H), 1.77–2.68 (broad m, 4H), 3.63 (s) over 3.28–3.92 (m) (total 4H), 4.05–4.72 (broad m, 2H) overlapped by water peak at 4.68.

EXAMPLE 13

N-(1-Carboxyethyl)-L-alanyl-L-proline

Dissolve 45 g of benzyl pyruvate and 4.5 g of L-alanine in a mixture of 115 ml of water and 250 ml of p-dioxane. Adjust the pH to 5.5 with NaOH. Add 9.4 g of sodium cyanoborohydride and stir at room temperature for 6 days. Adjust to pH 1 with conc. HCl.

Charge this solution to a column of Dowex 50 (H+) prepared in 50% dioxane-water. Wash with 50% dioxane-water, then with water. Elute the product with 2% pyridine in water; combine the product fractions and concentrate to dryness in vacuo. Triturate the solid residue with water, filter, and wash with water. Dry to obtain 6.8 g of N-(1-carbobenzoxyethyl)-L-alanine as a mixture of diastereoisomers. A second crop of 1.0 g can be obtained from the mother liquor solids.

Dissolve 208 mg of the above and 217 mg of L-proline benzyl ester hydrochloride in dry DMF. Cool to 0°. Add 0.193 ml of diphenylphosphoryl azide dissolved in DMF. Then add dropwise over 10 minutes a solution of 0.24 ml triethylamine in DMF holding the temperature at 0°. Stir 3 hours at 0°, then overnight at room temperature.

Dilute the mixture with ethyl acetate, wash with water and 5% sodium bicarbonate. Concentrate in vacuo to a small volume and chromatograph on a preparative silica tlc plate, developing with ethyl acetate. Scrape off the broad band at rf=0.5–0.6, elute with ethyl acetate, and strip off the solvent to obtain 212 mg of the mixture of diastereoisomers of N-(1-carbobenzoxyethyl)-L-alanyl-L-proline benzyl ester.

Dissolve 135 mg. of the above in a mixture of methanol and water. Add 50 mg of 10% Pd on C catalyst, and hydrogenate at 40 psi $H_2$ pressure and room temperature. Filter, concentrate in vacuo, and freeze dry to obtain 95 mg of the mixture of diastereoisomers of N-(1-carboxyethyl)-L-alanyl-L-proline. The nmr spectrum is comparable to that in Example 2 and the mass spectrum of the silylated derivative shows the same fragmentation pattern.

EXAMPLE 14

N-(1-Carboxyethyl)-L-alanyl-L-proline

Dissolve 0.75 g of N-(1-carbobenzoxyethyl)-L-alanine in pyridine and add 7.5 ml of 1 M triethylamine in pyridine. Cool, and add 1.09 g L-proline benzyl ester hydrochloride and 0.678 g dicyclohexylcarbodiimide. Store at 0° C. for 20 hours. Filter, then concentrate the reaction mixture in vacuo. Dissolve the residue in ethyl acetate and wash this solution with saturated $K_2CO_3$, then brine. Dry the organic phase, concentrate in vacuo, then chromatograph the residue on silica gel with ethyl acetate-hexane to isolate the diastereoisomeric mixture of N-(1-carbobenzoxyethyl)-L-alanyl-L-proline.

Hydrogenate in the usual manner with 10% Pd/C in aqueous ethanol and obtain, after work-up and freeze drying, N-(1-carboxyethyl)-L-alanyl-L-proline as a white solid.

nmr spectrum ($D_2O$): 1.65 ppm (d, 6H), 1.9–2.6 (M, 4H), 3.5–4.2 (M, 3H), 4.3–4.8 (M, 2H).

EXAMPLE 15

N-(1-Carbomethoxyethyl)-L-alanyl-l-proline

Neutralize a solution of 1.4 g of methyl L-alaninate HCl and 3.1 g of α-bromopropionic acid in a dioxane-water mixture to pH 9 with sodium hydroxide. Warm to 70° and hold for 30 minutes, keeping the pH at 8 to 9 by addition of sodium hydroxide as necessary. Cool, apply to a column of Dowex 50 (H+) ion exchange resin, wash with water, and elute with 2% pyridine in water. Combine the product fractions and freeze dry. Purify this crude by chromatography on an ion-exchange column of Dowex 50 (Na+) in 0.5 M sodium citrate buffer pH 3.3. Collect the product fractions, concentrate to a small volume in vacuo, and repeat the Dowex 50 (H+) chromatography. Freeze dry the product fractions to obtain the pure N-(1-carbomethoxyethyl)-alanine.

Couple this intermediate with L-proline-t-butyl ester using diphenylphosphoryl azide as described in Example 13, then remove the t-butyl ester by dissolving in trifluoroacetic acid at room temperature for 3 hours, distill off the TFA, and purify on a column of Dowex 50 (H+)-2% pyridine as described, to obtain N-(1-carbomethoxyethyl)-L-alanyl-L-proline as a mixture of diastereoisomers.

EXAMPLE 16

N-(1-Methoxycarbonyl-3-methylthiopropyl)-alanyl-L-proline

A solution of pyruvoyl-L-proline (185 mg), L-methionine methyl ester (600 mg), and sodium cyanoborohydride (200 mg) in 20 ml of methanol is adjusted to neutrality with dilute methanolic sodium hydroxide. After standing at room temperature for three days the product is absorbed on strong acid ion-exchange resin and eluted with 2% pyridine in water to yield 80 mg of product. The nmr spectrum shows $OCH_3$ at $3.95\delta$, $S-CH_3$ at $2.2\delta$ and $CH-CH_3$ at $1.55$ and $1.7\delta$. The mass spectrogram on silylated material shows the expected molecular ion at 404 m/e.

EXAMPLE 17

N-(1(S)-Carboxy-3-Methylthiopropyl)-alanyl-L-proline

A solution of N-(1(S)-methoxycarbonyl-3-methylthiopropyl)-DL-alanyl-L-proline (127.5 mg; 0.384 mM) in 2 ml of water is treated under nitrogen with 7.82 ml 0.100 N sodium hydroxide (0.782 mM) and stirred for 2½ hr. at room temperature. The product is absorbed from the reaction mixture onto 30 ml of Dowex 50 (H+) and eluted with 4% aqueous pyridine to yield 73.5 mg., which is further purified over a LH-20 column to yield 55.7 mg. of product. The nmr spectrum in $D_2O$ shows $S-CH_3$ at 2.1; $CH-\underline{CH}_3$ at 1.5 and $1.6\delta$ and no methyl ester. The mass spectrogram on silylated material shows the expected molecular ion at 462 m/e.

EXAMPLE 18

N-[1-Methoxycarbonyl-2-(3-indolyl)-ethyl]-alanyl-L-proline

In a manner similar to Example 16 tryptophan methyl ester is condensed with pyruvoyl-L-proline in the presence of sodium cyanoborohydride to yield N-[1-methoxycarbonyl-2-(3-indolyl)-ethyl]-alanyl-L-proline.

The nmr spectrum in $CDCl_3$ shows aromatic protons at 6.9 to 7.7; protons adjacent to the aromatic nucleus and adjacent to nitrogen at 2.8 to 3.9; aliphatic methylene protons at 1.4 to 2.7 and the alanine methyl at 1.0 to 1.4. The mass spectrogram on silylated material shows an ion at 516 m/e in accord with disilylated material having lost a $CH_3$ group.

EXAMPLE 19

N-[1(S)-carboxy-2-(3-indolyl)-ethyl]-DL-alanyl-L-proline

In a manner similar to Example 17 the product above is hydrolyzed to give the expected diacid. The nmr spectrum in $D_2O-d_5Pyr.$ shows 5 aromatic protons at 6.8 to 7.7; 7 protons adjacent to the aromatic nucleus and adjacent to nitrogen at 2.8 to 7.4 and 7 aliphatic protons at 1.0 to $2.2\delta$ in accord with the expected structure. The mass spectrogram on silylated material shows a peak at 431 m/e interpreted as a protonated monosilylated ion having lost a $CH_3$ group.

EXAMPLE 20

N-(1-Carboxy-3-phenylpropyl)-L-alanyl-L-4-thiazolidine carboxylic acid

Combine tBoc-Alanine (1.8 g) and L-thiazolidine-4-carboxylic acid benzyl ester hydrochloride (2.6 g) in methylene chloride. Treat at 0°-5° with triethylamine (1.4 ml), then with DCC (2.3 g) in methylene chloride and store overnight. After filtering and washing the filtrate with water and sodium bicarbonate solution, strip off the solvent and chromatograph on Silica G-60 (E. Merck) in ethyl acetate-hexane. Strip the solvent from the combined product fractions in vacuo. Hydrolyze the benzyl ester in acetonitrile-water at pH 13.5 (NaOH) for 1 hour at room temperature. Neutralize to pH 8 with HCl, wash with ether, concentrate the water layer in vacuo, freeze-dry. Remove the t-butyloxycarbonyl protecting group in 4 M hydrogen chloride in ethyl acetate, precipitate the product with ether, filter and dry to obtain the L-alanyl-L-thiazolidine-4-carboxylic acid. Condense 0.385 g of this with 1.88 g of 2-oxo-4-phenylbutyric acid in water using 0.354 g of sodium cyanoborohydride by the method described in Example 24, to obtain 0.53 g. of the mixture of diastereoisomers of N-(1-carboxy-3-phenylpropyl)-L-alanyl-L-4-thiazolidine carboxylic acid. The nmr spectrum ($D_2O+NaOD$) contains a split doublet at 1.2 ppm (3H), a singlet at 7.1 (5H), broad absorption in the 1.6 to 2.0 region (2H), and broad multiple absorptions in the 2.2 to 4.1 range and a large water peak at 4.6 ppm. The mass spectrum of silylated material shows the molecular ion of the disilylated derivative at m/e=556.

EXAMPLE 21

N-(1-Carboxy-3-phenylpropyl)-L-alanyl-L-pipecolinic acid

By substituting L-pipecolinic acid methyl ester hydrochloride (1.8 g) for the thiazolidine carboxylic ester of Example 20, the title compound can be prepared by the method described in that example.

The nmr spectrum ($CD_3OD$) shows a broad multiplet at 1.3–1.9 ppm (9H), a singlet at 7.22 (5H), and a series of multiplets in the 2.0–4.8 ppm range. The mass spectrum on silylated material exhibits a peak at m/e =580 for the disilylated molecular ion.

EXAMPLE 22

N-(1-Carboxy-3-phenylpropyl)-L-alanyl-L-N-methylalanine

By substituting L-N-methylalanine methyl ester hydrochloride (1.5 g) for the thiazolidine carboxylic ester of Example 20, one can prepare the title compound by the method described in that example.

EXAMPLE 23

N(1-Carboxy-1-methylethyl)-L-alanyl-L-proline

One can prepare the title compound by combining 7.7 g of 2-bromoisobutyric acid benzyl ester, 2.4 g of L-alanyl-L-proline t-butyl ester, and 7.0 g of silver oxide in 40 ml of benzene. After refluxing 24 hours, then adding an additional 7.7 g of the bromoester and 7.0 g of silver oxide, one continues to reflux for an additional 24 hours. Cooling, filtering, stripping off the solvent, one isolates the diester of the product by the usual chromatographic procedures. Removing the t-butyl ester group in trifluoroacetic acid and the benzyl group by catalytic hydrogenolysis in the established manner, one obtains the desired free acid.

EXAMPLE 24

N-(1-Carboxy-3-phenylpropyl)-L-alanyl-L-proline

A mixture of 4-phenyl-2-oxobutyric acid (1.49 g) and L-alanyl-L-proline (0.31 g) in water are adjusted to pH 7.5 with caustic and treated with sodium cyanoborohydride (0.32 g) overnight. The product is absorbed on strong acid ion exchange resin and eluted with 2% pyridine in water to give 0.36 g of crude diastereomeric product, N-(1-carboxy-3-phenylpropyl)-L-alanyl-L-proline. A portion is purified by gel filtration (LH-20) for spectrographic analysis. The nmr spectrum in DMSO shows aromatic hydrogen at 7.20, a broad singlet at 4.30, broad multiplets at 3.0 to 3.9, 2.67 and 1.94, and a doublet at 1.23 and 1.15. The mass spectrum shows a molecular ion at 492 m/e for the ditrimethylsilylated species.

EXAMPLE 25

N-(1-Carboxy-3-phenylpropyl)-L-alanyl-L-proline

Mill and sieve XAD-2 polystyrene resin (Rohm & Haas Co.). Define the 200–400 mesh fraction and charge 440 ml to a chromatographic column. Equilibrate with 0.1 M NH$_4$OH in 95:5 (v/v) water-methanol. Charge to the column 350 mg of N-(1-carboxy-3-phenylpropyl)-L-alanyl-L-proline, prepared and purified as described in Example 24, dissolved in 10 ml of the same solvent. Elute with this solvent. The first isomer emerges from the column in the volume range 375–400 ml of eluant. The second isomer in the range 440–480 ml, with the intermediate fractions containing a mixture of the isomers. Freeze dry the fraction containing the first isomer to obtain 130 mg of white solid. Recrystallize from 1 ml of water adjusted to pH 3 to obtain 94 mg of white needles, m.p. 148°–151° d. This is the more active isomer and has the S,S,S configuration as determined by X-ray analysis. $[\alpha]_D = -67.0°$, (0.1 M HCl) after drying in vacuo over P$_2$O$_5$. The nmr (DMSO) shows a single doublet for the methyl protons at 1.22 ppm. Freeze-dry the fraction containing the second isomer to obtain 122 mg. of white solid. Recrystallize 103 mg. from 2.5 ml of water adjusted to pH 3 to obtain 64 mg of feathery white crystals, m.p. 140°–145° d, $[\alpha]_D = -101.6°$ (0.1 M HCl) after drying. The nmr (DMSO) shows the methyl doublet at 1.17 ppm.

EXAMPLE 26

N-(1(S)-Ethoxycarbonyl-3-phenylpropyl)-L-alanyl-L-proline

Ethyl 2-oxo-4-phenylbutyrate (1.03 g) and L-alanyl-L-proline (0.19 g) are dissolved in a 1:1 ethanol-water solvent. A solution of sodium cyanoborohydride (0.19 g) in ethanol-water is added dropwise at room temperature over the course of two hours. When reaction is complete, the product is absorbed on strong acid ion-exchange resin and eluted with 2% pyridine in water. The product-rich cuts are freeze dried to give 0.25 g of crude N-(1-ethoxycarbonyl-3-phenylpropyl)-L-alanyl-L-proline. The mass spectrum shows a molecular ion at 448 m/e for the monosilylated species. Chromatography affords the desired isomer.

EXAMPLE 27

N-(1-Aminocarbonyl-3-phenylpropyl)-L-alanyl-L-proline

In the manner described in example 26, one can condense 2-oxo-4-phenylbutyramide and L-alanyl-L-proline in the presence of sodium cyanoborohydride to yield N-(1-amino carbonyl-3-phenylpropyl)-L-alanyl-L-proline.

EXAMPLE 28

N-(1-Carboxy-3-phenylpropyl)-L-alanyl-L-tryptophan

In the manner described in example 24, one can condense 2-oxo-4-phenylbutyric acid and L-alanyl-L-tryptophan in the presence of sodium cyanoborohydride to yield N-(1-carboxy-3-phenylpropyl)-L-alanyl-L-tryptophan.

EXAMPLE 29

N-(1-Carboxy-3-phenylpropyl)-L-alanyl-L-4-hydroxyproline

In the manner described in Example 24, 2-oxo-4-phenylbutyric acid and L-alanyl-L-4-hydroxyproline are condensed in the presence of sodium cyanoborohydride to yield N-(1-carboxy-3-phenylpropyl)-L-alanyl-L-4-hydroxyproline.

The nmr spectrum in deuteromethanol exhibits a doublet centered at 1.53 ppm (3H), a singlet at 7.13 (5H), and a series of multiplets in the range 2.0 to 4.7 ppm. The mass spectrum of silylated material shows the molecular ion of the trisilylated product at m/e =580.

EXAMPLE 30

N-(1-Carboxy-3-phenylpropyl)-L-serinyl-L-proline

In the manner described in example 24, 2-oxo-4-phenylbutyric acid and L-serinyl-L-proline are condensed in the presence of sodium cyanoborohydride to yield N-(1-carboxy-3-phenylpropyl)-L-serinyl-L-proline.

The mass spectrum shows a molecular ion at 580 m/e for the trisilylated species. The nmr spectrum in D$_2$O is consistent with structure.

EXAMPLE 31

N-(1-Carboxy-3-phenylpropyl)-L-phenylalanyl-L-proline

In the manner described in example 24, 2-oxo-4-phenylbutyric acid and L-phenylalanyl-L-proline are condensed in the presence of sodium cyanoborohydride to yield N-(1-carboxy-3-phenylpropyl)-L-phenylalanyl-L-proline.

The mass spectrum shows an ion at 406 m/e for the molecular ion minus water (424–18). The nmr spectrum in $D_2O$ was consistent with structure.

EXAMPLE 32

N-(1-Carboxy-3-phenylpropyl)-L-cysteinyl-L-proline

In the manner described in example 24, one can condense 2-oxo-4-phenylbutyric acid and L-S-benzyl-cysteinyl-L-proline in the presence of sodium cyanoborohydride. The product can then be treated with sodium in liquid ammonia to yield N-(1-carboxy-3-phenylpropyl)-L-cysteinyl-L-proline.

EXAMPLE 33

N-(1-Carboxy-3-phenylpropyl)-L-histidinyl-L-leucine

In the manner described in example 24, one can condense 2-oxo-4-phenylbutyric acid and L-histidinyl-L-leucine in the presence of sodium cyanoborohydride to yield N-(1-carboxy-3-phenylpropyl)-L-histidinyl-L-leucine.

EXAMPLE 34

N-(1-Carboxy-3-phenylpropyl)-L-phenylalanyl-L-arginine

In the manner described in example 24, one can condense 2-oxo-4-phenylbutyric acid and L-phenylalanyl-L-arginine in the presence of sodium cyanoborohydride to yield N-(1-carboxy-3-phenylpropyl)-L-phenylalanyl-L-arginine.

EXAMPLE 35

N-(1-Carboxy-3-phenylpropyl)-L-phenylalanyl-L-tryptophan

In the manner described in example 24, one can condense 2-oxo-4-phenylbutyric acid and L-phenylalanyl-L-tryptophan in the presence of sodium cyanoborohydride to yield N-(1-carboxy-3-phenylpropyl)-L-phenylalanyl-L-tryptophan.

EXAMPLE 36

N-[1-Carboxy-3-(3-indolyl)propyl]-L-alanyl-L-proline

In the manner described in example 24, 4-(3-indolyl)-2-oxobutyric acid and L-alanyl-L-proline are condensed in the presence of sodium cyanoborohydride to yield N-[1-carboxy-3-(3-indolyl)propyl]L-alanyl-L-proline. The mass spectrum of the trisilyated material shows a molecular ion at 603 m/e and a $M^+ - 15$ peak at 588 m/e.

EXAMPLE 37

N-(1-Carboxy-3-phenylpropyl)-L-alanyl-3,4-dehydroproline

Stir a mixture of 3,4-dehydroproline (2.3 g), t-Boc-L-alanine N-hydroxysuccinimide ester (7.2 g) and sodium carbonate (2.5 g) in a dioxane-water mixture at 0° overnight. Neutralize to pH 8 with HCl. Concentrate to a small volume in vacuo and freeze-dry. Remove the t-Boc protecting group with trifluoracetic acid in the usual manner and chromatograph on Dowex-50 (H+), eluting with 2% pyridine in water as described in example 2. Isolate the dipeptide by freeze-drying. Couple this product with 2-keto-4-phenylbutyric acid in the manner described in example 24 to obtain the product as a mixture of diastereoisomers. The mass spectrum shows a molecular ion at 490 m/e for the disilylated species.

The diastereomeric (140 mg) produced above is separated into its components by chromatography on XAD-2 resin as described in Example 25. The major component (70 mg) is first off the column $\alpha_D - 143°$ (c=1.3 methanol). The mass spectrum of each component shows a molecular ion at 490 m/e for ditrimethylsilylated species.

EXAMPLE 38

N-(1-Carboxy-3-phenylpropyl)-L-alanyl-2-methyl-thiazolidine-4-carboxylic acid

One can prepare this compound in the manner described in Example 37 by substituting 2.9 g of 2-methylthiazolidine-4-carboxylic acid for the 2.3 g of 3,4-dehydroproline.

EXAMPLE 39

N-(1-Carboxy-3-phenylpropyl)-L-alanyl-2-methylalanine

One can prepare this compound in the manner described in example 37 by substituting 1.8 g of 2-methylalanine for the 2.3 g of 3,4-dehydroproline.

EXAMPLE 40

Dry filled capsules containing 50 mg. of active ingredient per capsule

|  | Per Capsule |
| --- | --- |
| N—(1-carboxy-2-phenylethyl)-L-alanyl-L-proline | 50 mg. |
| Lactose | 149 mg. |
| Magnesium Stearate | 1 mg. |
| Capsule (Size No. 1) | 200 mg. |

The N-(1-carboxy-2-phenylethyl)-L-alanyl-L-proline is reduced to a No. 60 powder and then lactose and magnesium stearate are passed through a No. 60 bolting cloth onto the powder and the combined ingredients admixed for 10 minutes and then filled into a No. 1 dry gelatin capsule.

EXAMPLE 41

N-(1-Ethoxycarbonyl-3-Phenylpropyl)-L-Alanyl-L-Proline

A solution of L-alanyl-L-proline (7.7 g) and ethyl 2-oxo-4-phenylbutyrate (42.6 g) in 140 ml of ethanol is stirred with 64 g of powdered molecular sieves at room temperature for 0.5 hr. A solution of sodium cyanoborohydride (2.6 g) in 40 ml ethanol is then added slowly over the course of 6 hours. After filtering off the sieves the reaction mixture is concentrated under vacuum to a small volume. The residue is distributed between $CHCl_3$ and water. The pH is adjusted to 8.5 and the $CHCl_3$ layer is separated and discarded. The aqueous layer is acidified to pH 2.7, and the product is extracted into chloroform. The chloroform extract is dried over $Na_2SO_4$ and concentrated under vacuum to yield 10.4 g of mixed diastereomers. HPLC indicates the major product is the desired N-(1-(S)-ethoxycarbonyl-3-phenylpropyl)-L-alanyl-L-proline.

The nmr spectrum showed aromatic absorption at 7.1δ and diasteromeric methyls as a multiplet centered at 1.3δ.

The mass spectrum showed a molecular ion at 376 m/e and a strong peak at 358 m/e (M+ −H$_2$O).

EXAMPLE 42

N-(1(S)-Ethoxycarbonyl-3-phenylpropyl)-L-alanyl-L-proline maleate salt

A solution of N-(1-ethoxycarbonyl-3-phenylpropyl-L-alanyl-L-proline, mixed isomers (13.8 g), in 69 ml of acetonitrile is treated with 4.25 g of maleic acid in 69 ml of acetonitrile. After stirring for 1 hr. at room temperature, the solid is filtered, washed with acetonitrile and air dried to yield 8.4 g of maleate salt, m.p. 141°–145°, by HPLC ca 96% pure. The crude maleate salt is recrystallized from acetonitrile to yield 7.1 g of N-(1(S)-ethoxycarbonyl-3-phenylpropyl)-L-alanyl-L-proline maleate salt, m.p. 148°–150°, by HPLC ca 99% pure.

EXAMPLE 43

A.

N-(1-Ethoxycarbonyl-3-phenylpropyl)-L-alanyl-L-proline

A mixture of 0.814 g of L-alanyl-L-proline, 0.206 g of ethyl 2-oxo-4-phenylbutyrate, and 1.6 g of molecular sieves in 10 ml ethanol is hydrogenated at room temperature under 40 pounds pressure with 0.1 g of 10% Pd on carbon as catalyst. After uptake of hydrogen ceases the crude product obtained by filtration and concentration is absorbed on ion exchange resin, (Dowex 50, H+) and eluted with 2% pyridine in water to yield 0.224 g of N-(1-ethoxycarbonyl-3-phenylpropyl)-L-alanyl-L-proline. HPLC indicates a 55:45 isomer ratio.

B.

N-[1(S)-Ethoxycarbonyl-3-phenylpropyl]-L-alanyl-L-proline maleic acid salt

A mixture of 3 g. of L-alanyl-L-proline, 5 g of ethyl 2-oxo-4-phenyl-butanoate, 13 g. of 3A molecular sieves, and 3.6 g. of Raney nickel in 85 ml of ethanol is hydrogenated at 25° C. and at 40 psig of hydrogen until uptake of hydrogen ceases. The solids are filtered, washed with 80 ml. of ethanol and the filtrates are combined. Assay by high pressure liquid chromatography shows an 87:13 ratio of diastereoisomers in favor of the desired product. Ethanol is removed under vacuum to afford an oil which is dissolved in 60 ml. of water and 20 ml. of ethyl acetate. The pH of the stirred two-phase mixture is adjusted to 8.6 with 50% NaOH. The layers are separated and the water phase is extracted with 2×20 ml more of ethyl acetate. The water phase is adjusted to pH 4.25 with hydrochloric acid, 12 g. of NaCl is dissolved in the water, and product is extracted with 5×12 ml of ethyl acetate. The extracts are combined and dried with Na$_2$SO$_4$. The desired product, N-[1-(S)-ethoxycarbonyl-3-phenylpropyl]-L-alanyl-L-proline, is crystallized as its maleate salt by addition of 1.86 g. of maleic acid. After stirring for 4 hours, the salt is filtered, washed with ethyl acetate and dried to afford 5.2 g. of pure product, m.p. 150°–151° C.

EXAMPLE 44

N-(1-Benzyloxycarbonyl-3-phenylpropyl)-L-alanyl-L-proline

A solution of L-alanyl-L-proline (167 mg) and benzyl 2-oxo-4-phenylbutyrate (1.20 g) in 5 ml of ethanol is stirred at room temperature with 3 g of powdered molecular sieves, type 4A. Sodium cyanoborohydride (75 mg) is then added in portions over the course of three hours. The product is purified by absorption on strong cation exchange resin and elution with 2% pyridine in water. After passage through a gel filtration (LH-20) column 220 mg of N-(1-benzyloxycarbonyl-3-phenylpropyl)-L-alanyl-L-proline is obtained as a mixture of isomers. Thin layer chromatography on silica gel eluted with 1 EtOAc, 1 n-butanol, 1 H$_2$O, 1 HOAc shows one main post, R$_f$ 0.71. Isomers are separated using reverse phase HPLC to yield N-(1(S)-benzyloxycarbonyl-3-phenylpropyl)-L-alanyl-L-proline.

In a similar fashion N-acetylaminoethyl-2-oxo-4-phenylbutyrate and L-alanyl-L-proline when reduced with sodium cyanoborohydride gives N-[1-(2-acetylamino)ethoxycarbonyl-3-phenylpropyl]-L-alanyl-L-proline.

Similarly dimethylaminoethyl 2-oxo-4-phenylbutyrate and L-alanyl-L-proline gives N-[1-(2-dimethylamino)-ethoxycarbonyl-3-phenylpropyl]-L-alanyl-L-proline.

Similarly, benzyl 2-oxo-5-methylhexanoate and L-alanyl-L-proline give N-(1-benzyloxycarbonyl-4-methylpentyl)-L-alanyl-L-proline.

The mass spectrum of silylated material gave peaks at 510 (M+, very weak), 495 (M+ −15), 464,420,419,385 and 296 m/e (base peak).

The nmr spectrum was consistant with structure.

EXAMPLE 45

N-(1-Butoxycarbonyl-3-phenylpropyl)-L-alanyl-L-proline

A solution of N-benzyloxycarbonyl-L-alanyl-L-proline 3° butyl ester (452 mg) in 5 ml of benzene is hydrogenated over 150 mg of 10% Pd on carbon to remove the nitrogen protecting group. After filtration and evaporation of the solvent, the L-alanyl-L-proline 3° butyl ester is dissolved in 8 ml of tetrahydrofuran and treated with 1.41 g of butyl 2-oxo-4-phenylbutyrate and 3 g of powdered molecular sieves. Sodium cyanoborohydride (150 mg) is added in portions over the course of several hours, and the mixture stirred at room temperature overnight. After filtration and concentration under vacuum the residue is treated with 25 ml of trifluoroacetic acid at room temperature for 2 hours. After removal of the acid the product is purified by absorption on ion exchange resin and by gel filtration (LH-20). Concentration and drying of product rich cuts affords 182 mg of N-(1-butoxycarbonyl-3-phenylpropyl)-L-alanyl-L-proline as a mixture if isomers. Thin layer chromatography (silica gel, 1 EtOAc, 1 butanol, 1 H$_2$O, 1 HOAc) shows two spots, R$_f$ 0.67 and 0.72. The mass spectrum shows peaks at 548 (disilylated molecular ion) and 476 (monosilylated molecular ion). Isomers are separated using reverse phase HLPC to yield N-(1(S)-butoxycarbonyl-3-phenylpropyl)-L-alanyl-L-proline.

EXAMPLE 46

N-(1-Ethoxycarbonyl-3-phenylpropyl)-L-alanyl-L-proline ethyl ester

A solution of 0.63 g of N-(1-carboxy-3-phenylpropyl)-L-alanyl-L-proline in 9.7 ml of ethanol is saturated with HCl gas at 0°. After standing overnight at room temperature the HCl and ethanol is removed under vacuum to yield a light yellow oil which is purified by gel filtration (LH-20 column). The yield of N-(1-ethoxycarbonyl-3-phenylpropyl)-L-alanyl-L-proline ethyl ester is 0.39 g, one spot by thin layer chromatography. The nmr spectrum indicates two ethyl groups per aromatic ring. The mass spectrum shows a molecular ion at 404 m/e.

EXAMPLE 47

N-(1-Carboxy-3-phenylpropyl)-L-alanyl-trans-4-methoxy-L-proline

Prepare methyl trans-4-methoxy-L-prolinate hydrochloride from L-hydroxyproline by the method of E. Adams et al., J. Biol. Chem., 208, 573 (1954), esterifying with methanolic hydrogen chloride in the standard manner. Couple with Boc-L-alanine in methylene chloride with dicyclohexylcarbodiimide as previously described, purifying the intermediate Boc-L-Ala-L-methoxy Pro-OMe by chromatography on silica gel, eluting with ethyl acetate:hexane 1:1. Hydrolyze the ester with sodium hydroxide in acetonitrile-water, adjust the pH to 7.5, freeze dry, and deprotect the amine in 4 M hydrogen chloride in ethyl acetate in the usual manner. Condense 0.54 g of this L-alanyl-trans-4-methoxy-L-proline with 2.0 g of 2-oxo-4-phenylbutyric acid in 6 ml of water, employing 0.43 g of sodium cyanoborohydride in the manner described in Example 24. Isolate as described in that example to obtain 0.92 g of a mixture of diastereoisomers of N-(1-carboxy-3-phenylpropyl)-L-alanyl-trans-4-methoxy-L-proline.

The nmr spectrum in $D_2O$ shows a split doublet centered at 1.58 ppm (3H), singlets at 3.37 (3H) and 7.35 ppm (5H), complex absorption in the 1.9–3.5 region and a broad multiplet at 4.0–4.6 ppm. The mass spectrum shows prominent peaks at m/e=360 (M−18) and 256 (M−122).

EXAMPLE 48

N-(1-Benzyloxycarbonyl-3-phenylpropyl)-L-alanyl-trans-4-methoxy-L-proline

By coupling L-alanyl-L-4α-methoxyproline, prepared as in Example 47 above, with benzyl 2-oxo-4-phenylbutyrate in ethanol using sodium cyanoborohydride by the method described in Example 44, one can obtain the mixture if diastereosimers of N-(1-benzyloxycarbonyl-3-phenylpropyl)-L-alanyl-trans-4-methoxy-L-proline. Isomers can then be separated using reverse phase HPLC to yield N-(1(S)-benzyl-oxycarbonyl-3-phenylpropyl)-L-alanyl-trans-4-methoxy-L-proline.

EXAMPLE 49

N-(1-Benzylaminocarbonyl-3-phenylpropyl)-L-alanyl-L-proline

Prepare the benzylamide of 2-oxo-4-phenylbutyric acid by dissolving 3.0 g of this acid, 2.4 ml of benzylamine, and 4.7 ml of diphenylphosphorylazide in 60 ml of cold dimethylformamide and adding dropwise 2.6 ml of triethylamine in DMF, holding the temperature at about −10° C. for 2.5 hours. Store overnight at room temperature, strip off the DMF in vacuo, and partition the residue between water and ethyl acetate. Chromatograph the contents of the organic layer on silica gel, eluting with ethyl acetate:hexane 1:4. Evaporate the solvent from the product fractions to obtain 2.2 g of crystalline n-benzyl-2-oxo-4-phenylbutyramide. Couple 1.26 g of this with 0.19 g of L-Ala-L-Pro using 0.125 g of sodium cyanoborohydride in ethanol in the manner described in Example 44. Purify the crude product by gel filtration (LH-20) to obtain the mixture of diastereoisomers of N-(1-benzylaminocarbonyl-3-phenylpropyl)-L-alanyl-L-proline. The nmr spectrum ($CDCl_3$) shows a doublet at 1.1 ppm (3H) a close pair of singlets at 7.3 (10H), and complex absorption at 1.6–2.3 (6H), 2.3–2.9 (2H), 2.9–3.8 (4H) and 4.0–4.6 (3H). The mass spectrum of silylated material shows prominent peaks at m/e=509 (monosilyl derivative) and 581 (disilyl derivative).

EXAMPLE 50

N-(1-Carboxy-3-phenylpropyl)-L-alanyl-L-N-methylphenylalanine

By substituting N-methyl-L-phenylalanine methyl ester for the thiazolidine carboxylic ester of Example 20, prepare L-alanyl-N-methyl-L-phenylalanine. Condense 0.85 g of this with 3.02 g of 2-oxo-4-phenylbutyric acid employing 0.64 g of sodium cyanoborohydride in water as described. Acidify the mixture to pH 1.5 and extract into ether. Strip off the ether, dissolve the residue in 70% methanol-water, and chromatograph on Dowex 50 ($H^+$) made up in that solvent, eluting with a solution of 3% pyridine in the same solvent mixture. Combine product fractions, concentrate, freeze-dry, and purify on LH-20 in methanol to obtain 0.54 g of the mixture of isomers of N-(1-carboxy-3-phenylpropyl)-L-alanyl-L-N-methylphenylalanine. The nmr spectrum ($D_2O$, NaOD) exhibits a doublet centered at 1.18 ppm (3H), two overlapping singlets at 7.3 (10 H), a singlet at 2.95 (3H), and broad multiple absorptions in the 1.4 to 2.1 and 2.3 to 4.4 ranges. The mass spectrum of silylated material shows the molecular ion of the disilylated material at m/e=556.

EXAMPLE 51

N-(1-Ethoxycarbonyl-3-phenylpropyl)-L-alanyl-L-proline amide

Prepare L-alanyl-L-proline amide by coupling t-Boc-L-alanine with L-proline amide by established methods employing dicyclohexylcarbodiimide in 4:1 methylene chloroform:DMF. Purify the intermediate t-Boc-L-Ala-L-Pro-$NH_2$ by chromatography on LH-20 in methanol, then remove the t-Boc protecting group in 4 M HCl in ethyl acetate. Couple 0.5 g of this L-Ala-L-Pro-$NH_2$.HCl in 10 ml of absolute ethanol neutralized with an equivalent of triethyl amine with 2.4 g of ethyl 2-oxo-4-phenylbutyrate using molecular sieves and 0.30 g of sodium cyanoborohydride as described in Example 41. In this present example the product is found in the chloroform extract at pH 8.5; concentrate it in vacuo, dissolve in 50% ethanol-water, chromatograph on Dowex 50 ($H^+$) made up in 50% ethanol-water, and elute with 2% pyridine in this solvent. Combine the product fractions, and purify further by chromatography on LH-20 in methanol. Strip off the solvent in vacuo to obtain 0.40 g of N-(1-ethoxycarbonyl-3-phenylpropyl)-L-alanyl-L-proline amide as a mixture of diastereoisomers. The nmr spectrum (CDCl₃) exhibits a triplet overlapping a doublet at 1.1–1.5 ppm (6H), a series of five multiplets in the range 1.5–4.7 ppm (15H) and a singlet at 7.17 ppm (5H). The mass spectrum on silylated material shows prominent peaks at m/e=477 (monosilyl derivative) and 519 (disilyl derivative).

EXAMPLE 52

N-(1-Carboxy-3-phenylpropyl)-L-alanyl-L-proline amide

Couple L-alanyl-L-proline amide, prepared as in Example 51, with 2-oxo-4-phenylbutyric acid employing sodium cyanoborohydride in 50% ethanol-water by the method described in example 2. After eluting from the ion-exchange resin, concentrate in vacuo to a small volume, flush with water, and freeze-dry to obtain N-(1-carboxy-3-phenylpropyl)-L-alanyl-L-proline amide as a mixture of diastereoisomers.

The nmr spectrum showed aromatic absorption at 7.35δ and a pair of doublets for diastereomeric methyls at 1.55δ.

EXAMPLE 53

N-(1(S)-hydroxyaminocarbonyl-3-phenypropyl)-L-alanyl-L-proline

To a cold solution of 0.19 g of N-(1-ethoxycarbonyl-3-phenylpropyl)-L-alanyl-L-proline maleate salt, prepared as in Example 42, in 1 ml of ethanol, add 0.85 g of potassium hydroxide in 0.57 ml of ethanol. Then add dropwise a suspension of 0.07 g of hydroxylamine hydrochloride in 0.9 ml of ethanol containing 0.060 g of potassium hydroxide. Hold in an ice bath for two hours, then at room temperature overnight. Decant the supernatant, dilute with 10 ml of water, adjust the pH to 2.5 with hydrochloric acid, and wash with chloroform. Neutralize and freeze-dry the aqueous layer and purify by chromatography on XAD-2 resin in a gradient of 0.1 M ammonium hydroxidemethanol to obtain the N-(1(S)-hydroxyaminocarbonyl-3-phenylpropyl)-L-alanyl-L-proline. The mass spectrum of silylated material shows an ion at m/e=579 for the trisilylated derivative, and the nmr is consistant with the structure.

EXAMPLE 54

N-(1-Carboxy-3-methylbutyl)-L-alanyl-L-tryptophan

A solution of the sodium salt of 4-methyl-2-oxopentanoic acid (414 mg) and L-alanyl-L-tryptophan (150 mg) in water are adjusted to pH 7 with caustic and treated with sodium cyanoborohydride (103 mg) at room temperature for several days. The product is adsorbed on strong acid ion exchange resin and eluted with 2% pyridine in water. The product rich cuts are freeze dried affording 189 mg of fluffly white solid. The mass spectrum shows a molecular ion at 389 m/e and peaks at 187 m/e and 158 m/e for the fragments shown respectively:

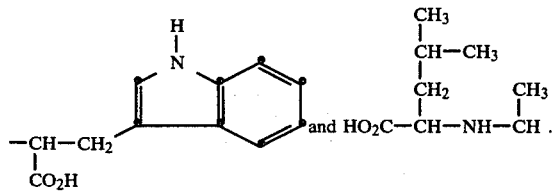

The nmr spectrum in D₂O is consistent with structure.

EXAMPLE 55

N-(1-Carboxy-3-methylbutyl)-L-histidyl-L-leucine

In the manner decribed in Example 54, 4-methyl-2-oxopentanoic acid and L-histidyl-L-leucine are condensed in the presence of sodium cyanoborohydride to yield N-(1-carboxy-3-methylbutyl)-L-histidyl-L-leucine. In this case the product is eluted from the ion exchange resin with 10% ammonia. The mass spectrum shows a molecular ion at 408 m/e for the disilylated species minus 18. The nmr spectrum is consistent with structure.

EXAMPLE 56

N-(1-Carboxy-3-methylbutyl)-L-phenylalanyl-L-arginine

In the manner described in Example 54, 4-methyl-2-oxopentanoic acid and L-phenylalanyl-L-arginine are condensed in the presence of sodium cyanoborohydride to yield N-(1-carboxy-3-methylbutyl)-L-phenylalanyl-L-arginine. The product is eluted from the ion exchange resin with 10% ammonia. The nmr spectrum in D₂O gave a singlet at 7.2 (5H), a broad triplet centered at 3.0 (6H), a broad multiplet at 1.3 (6H), and a broad doublet at 0.9 (6H).

EXAMPLE 57

A. N-(1-Carboxy-3-phenylpropyl)-L-lysyl-L-proline

In the manner described in Example 54, 2-oxo-4-phenylbutyric acid and -t-BOC-L-lysyl-L-proline are condensed in the presence of sodium cyanoborohydride. Essentially all of the -t-BOC protecting group is cleaved when the product is absorbed on strong acid ion exchange resin. The crude N-(1-carboxy-3-phenylpropyl)-L-lysyl-L-proline is eluted from the resin with 10% ammonia, freeze dried, and purified by gel filtration chromatography (LH-20). A minute peak for t-BOC protons in the nmr spectrum disappears when the product is treated with ethyl acetate that is 4 N in hydrogen chloride gas. The nmr spectrum of the resulting HCl salt of the product is consistent with structure. The mass spectrum shows a molecular ion at 693 m/e for the tetrasilylated species. Chromatography on XAD-2 resin using 3.5% acetonitrile in 0.1 molar ammonium hydroxide affords N-α-(1(S)-carboxy-3-phenylpropyl)-L-lysyl-L-proline.

B.

N-α-(1(S)-Carboxy-3-phenylpropyl)-L-lysyl-L-proline

In the manner described in Example 54, 2-oxo-4-phenylbutyric acid and N- -t-Boc-L-lysyl-L-proline are condensed in the presence of sodium cyanoborohydride. The product is absorbed on strong acid ion exchange resin, and eluted with 2% pyridine in water. Product-rich cuts are stripped to a glass and treated with 4 N HCl in ethylacetate to remove the t-Boc protecting group. The resulting hydrochloride salt is converted to the free base by absorbing on strong acid ion exchange resin and eluting with 2% pyridine in water. Freeze drying of product-rich cuts affords N-α-(1-carboxy-3-phenylpropyl)-L-lysyl-L-proline as a white fluffy solid. The nmr spectrum is consistent with structure. The mass spectrum shows a molecular ion at 549 for the disilylated species. Chromatography affords the desired isomer.

EXAMPLE 58

N-(1-Carboxy-3-phenylpropyl)-L-3-fluoroalanyl-L-proline

To a solution of L-3-fluoroalanine (420 mg) in 4 ml acetone-water (1:1) is added triethylamine (590 mg) and 2-t-butoxycarbonyloximino-2-phenylacetonitrile (1.060 g). The mixture is stirred 2.5 hr. Cold 5% aqueous potassium bicarbonate solution is added and the mixture is extracted with ethyl acetate. The aqueous phase is acidified with cold 1 N hydrochloric acid and extracted with ethyl acetate. The latter extract is washed with saturated aqueous sodium chloride, dried over sodium sulfate and concentrated to dryness to give L-t-BOC-3-fluoroalanine (800 mg), m.p. 91°–93°.

To a stirred solution of the latter (800 mg) and proline benzyl ester (1.5 g) in methylene chloride (8 ml) at 0° is added dicyclohexylcarbodiimide (845 mg) in methylene chloride (6 ml) and the mixture is kept at 0° for 2 hr and 20° for 18 hr. The mixture is filtered, the precipitate washed with methylene chloride and the combined filtrate and washings extracted with cold 1 N hydrochloric acid, cold 5% aqueous potassium bicarbonate, saturated aqueous sodium chloride, dried over sodium sulfate and concentrated to dryness. Dry column chromatography on silica gel H eluting with 6% acetone in chloroform gives the pure protected dipeptide.

The t-boc group is removed by treatment with 4 N hydrogen chloride in ethyl acetate (8 ml) at 0° for 1 hr. Ether (~20 ml) is added and the precipitated L-3-fluoroalanyl-L-proline benzyl ester hydrochloride (450 mg), m.p. 158°–161°, is collected by filtration. Hydrogenation in 6 ml water and 2 ml ethanol over 60 mg of 10% palladium on charcoal at 1 atmosphere pressure and 20° C. for 90 minutes followed by filtration and concentration to dryness yields L-3-fluoroalanyl-L-proline hydrochloride (330 mg). The mass spectrum shows a molecular ion at 348 m/e for the ditrimethylsilylated species.

To a mixture of 4-phenyl-2-oxobutyric acid (375 mg) and L-fluoroalanyl-L-proline hydrochloride (100 mg) in 3 ml of water (pH adjusted to 7 with sodium hydroxide) is added sodium cyanoborohydride (80 mg). The mixture is stirred 20 hr. and worked up as described in Example 24. The mass spectrum of the LH-20 purified product shows a molecular ion at 510 m/e for the ditrimethylsilylated species; tlc-silica gel plate single spot $R_F=0.7$—system 1:1:1:1 ethyl acetate:acetic acid:n-butanol:water.

The diastereomers are separated on XAD-2 resin as described in Example 25.

N-(1-ethoxycarbonyl-3-phenylpropyl)-L-3-fluoroalanyl-L-proline is prepared as described in Example 26.

EXAMPLE 59

N-(1-Ethoxycarbonyl-3-phenylpropyl)-L-alanyl-L-3,4-dehydroproline

By the procedure of Example 26 L-alanyl-L-3,4-dehydroproline produced as in Example 37 is converted into N-(1-ethoxycarbonyl-3-phenylpropyl)-L-alanyl-L-3,4-dehydroproline as a two component diastereomeric mixture, tlc-silica gel plate $R_F$ 0.82 (major) and $R_f$ 0.79 (minor), two developments in the system 4:1:1—n-butanol:water:acetic acid. The mass spectrum shows a molecular ion at 518 m/e for the ditrimethylsilylated species.

EXAMPLE 60

N-[1(S)-Methoxycarbonyl-2-(1H-imidazol-4-yl)-ethyl]-DL-alanyl-L-proline

In a manner similar to Example 16, L-histidine methyl ester is condensed with pyruvoyl-L-proline in the presence of sodium cyano borohydride to yield N-[1-methoxycarbonyl-2-(1H-imidazol-4-yl)ethyl]-DL-alanyl-L-proline. The nmr spectrum in $D_2O$ shows the imidazole protons at 8.6 and 7.3; the protons adjacent to the imidazole and the methyl ester protons at 3.7 and the alanyl methyl at 1.1 to 1.38.

EXAMPLE 61

N-[1(S)-Carboxy-2-(1H-imidazol-4-yl)-ethyl]-DL-alanyl-L-proline

In a manner similar to Example 17 the product from Example 60 is hydrolyzed to give the expected diacid. The nmr spectrum in $D_2O$ shows the imidazole protons at 7.2 and at 8.5; and the alanine methyl at 1.25δ.

EXAMPLE 62

N-(1(S)-Ethoxycarbonyl-5-aminopentyl)-D,L-alanyl-L-proline

A solution of ε-benzyloxycarbonyl-L-lysine ethyl ester hydrochloride (2.94 g.) in water (10 ml.) is made basic with 15 ml. of saturated aqueous potassium bicarbonate and extracted with $CH_2Cl_2$. The extract is dried over $MgSO_4$ and concentrated to dryness. The residue, ε-Benzyl oxycarbonyl-L-lysine ethyl ester, is dissolved in THF (20 ml.) and pyruvoylproline (555 mg.) and powdered No. 4A molecular sieves (1.0 g.) are added. The mixture is stirred at room temperature for 4 hours. Sodium cyanoborohydride (630 mg.) in 1 ml. of $CH_3OH$ is added over 2 hours and the mixture is stirred overnight. It is then filtered, concentrated to dryness, and the residue partitioned between water (10 ml.) and $CH_2Cl_2$ (15 ml.). The aqueous phase is absorbed on strong acid ion-exchange resin and eluted with 4% pyridine in water to yield 470 mg. of N-(1(S)-ethoxycarbonyl-5-benzyloxycarbonylaminopentyl)-D,L-alanyl-L-proline. The protecting group is removed by hydrogenation in ethanol-water 1:1 over 10% Pd/c catalyst at 40 ps.i. The mixture is filtered and the filtrate taken to dryness. The residue in methanol is chromatographed on an LH-20 column to give the desired N-(1(S)-ethoxycarbonyl-5-aminopentyl)-D,L-alanyl-L-proline. The mass spectrum of silylated material gave a peak at 559 m/e for the trisilylated derivative and a peak at 487 m/e for the disilylated derivative. The nmr ($D_2O$) confirmed the structure.

EXAMPLE 63

N-(1(S)-Carboxy-5-aminopentyl)-L-alanyl-L-proline

N-(1(S)-ethoxycarbonyl-5-benzyloxycarbonyl aminopentyl)-D,L-alanyl-L-proline, as prepared in Example 62, is treated with 0.1 M NaOH at room temperature overnight. After absorption of the product on strong acid ion-exchange resin, it is eluted with 4% pyridine in water to yield N-(1(S)-carboxy-5-benzyloxycarbonylaminopentyl)-D,L-alanyl-L-proline, single spot by tlc (Rf 0.4-butanol:water:pyridine:acetic acid 10:4:3:1). In a manner similar to Example 62, the protecting group is removed by hydrogenation to yield N-(1(S)-carboxy-5-aminopentyl)-D,L-alanyl-L-proline. The mass spectrum of the trimethylsilylated product is in accord with the structure, having a mass peak at 531 m/e. Chromatography affords the desired isomer.

EXAMPLE 64

N-(1-Carboxy-6-aminohexyl)-L-alanyl-L-proline

Benzyl 2-oxo-7-phthalimidoheptanoate (prepared by alkylation of benzyl 1,3-dithiane-2-carboxylate with 5-phthalimidopentyl bromide and subsequent oxidative conversion to the ketone with N-bromosuccinimide) is condensed with L-alanyl-L-proline in the presence of excess NaBH$_3$CN. The condensation product, N-(1-benzyloxycarbonyl-6-phthalimidohexyl)-L-alanyl-L-proline, (390 mg.) in 25 ml of 50% aqueous ethanol is hydrogenated at 40 psi over 10% palladium on charcoal. Removal of solvent and catalyst yields N-(1-carboxy-6-phthalimidohexyl)-L-alanyl-L-proline (320 mg) having the expected spectral and chromatographic properties. A portion of the above intermediate (152 mg) in 2 ml of ethanol is refluxed with hydrazine (32 mg) for 1.5 hours. The phthalhydrazide is removed by filtration; the ethanol is removed under vacuum and the residue is absorbed on strong acid ion-exchange resin. Elution with 2% aqueous pyridine and freeze-drying gives the desired N-(1-carboxy-6-aminohexyl)-L-alanyl-L-proline (58 mg.). The spectral data are consistent with structure. The mass spectrum shows a peak at 311 for the molecular ion minus water (329-18).

EXAMPLE 65

N-(1-Benzyloxycarbonyl-6-aminohexyl)-L-alanyl-L-proline

By performing the hydrazinolysis as described in Example 64 on N-(1-benzyloxycarbonyl-6-phthalimidohexyl)-L-alanyl-L-proline a mixture is obtained from which N-(1-benzyloxycarbonyl-6-aminohexyl)-L-alanyl-L-proline may be isolated. Thin layer chromatography on silica gel eluted with 50 BuOH: 11HOAC:30 H$_2$O gave a spot, R$_f$0.32.

EXAMPLE 66

N-(1-Carboxy-2-phenoxyethyl)-L-alanyl-L-proline

A slurry of phenoxypyruvic acid (1.8 g) (prepared by the condensation of ethyl phenoxyacetate with diethyl oxalate, followed by acid catalyzed hydrolysis and decarboxylation) and L-alanyl-L-proline (0.37 g) in 10 ml of water is adjusted to pH 7 with dilute NaOH. The mixture is treated with NaBH$_3$CN (0.18 g) and allowed to stir at room temperature for 5 days. On the second and third days additional ketoacid (0.9 g) and sodium cyanoborohydride (0.18 g) are added. The product is adsorbed on strong acid ion-exchange resin and eluted with 2% pyridine in water to yield, after freeze-drying, 0.5 g of N-(1-carboxy-2-phenoxyethyl)-L-alanyl-L-proline. The nmr is consistent with structure. The mass spectrum shows a peak at 479 for the silylated molecular ion minus methyl (494-15).

EXAMPLE 67

N-(1-Ethoxycarbonyl-2-phenoxyethyl)-L-alanyl-L-proline

By reacting ethyl phenoxy pyruvate (prepared from the acid by acid catalyzed esterification) and L-alanyl-L-proline with NaCNBH$_3$ in ethanol solution and isolating the product as described in Example 66, one can obtain N-(1-ethoxycarbonyl-2-phenoxyethyl)-L-alanyl-L-proline.

EXAMPLE 68

N-(1-Carboxy-2-phenylthioethyl)L-alanyl-L-proline

A mixture of phenylthiopyruvic acid (1.96 g) (prepared by the condensation of ethyl phenylthioacetate with diethyloxalate, followed by acid catalyzed hydrolysis and decarboxylation) and L-alanyl-L-proline (0.37 g.) in 10 ml H$_2$O is adjusted to pH 7.0 with dilute NaOH and treated with NaBH$_3$CN (0.18 g) in 2 ml H$_2$O. After stirring overnight at room temperature the product is absorbed on strong acid ion-exchange resin and eluted with 2% pyridine in water to yield 0.36 g. of N-(1-carboxy-2-phenylthioethyl)-L-alanyl-L-proline. The nmr and mass spectrum indicate the desired structure. A mass peak at 348 indicates the molecular ion (366)-water (18).

EXAMPLE 69

N-(1-Ethoxycarbonyl-2-phenylthioethyl)-L-alanyl-L-proline

By reacting ethyl phenylthiopyruvate (prepared from the acid by esterification) and L-alanyl-L-proline with NaBH$_3$CN in ethanol solution as described in Example 68 and isolating the product as described therein, one can obtain N-(1-ethoxycarbonyl-2-phenylthioethyl)-L-alanyl-L-proline.

EXAMPLE 70

N-(1-Ethoxycarbonyl-3-p-chlorophenylpropyl)-L-alanyl-L-proline

A solution of ethyl 4-p-chlorophenyl-2-oxobutyrate (prepared from the acid by esterification with ethanol in refluxing CCl$_4$) and L-alanyl-L-proline in ethanol can be treated with excess NaBH$_3$CN and stirred at room temperature until reaction is complete. The ethanol can then be removed under vacuum and the product absorbed on strong acid ion-exchange resin. By elution with 2% pyridine in water, one can obtain N-(1-ethoxycarbonyl-3-p-chlorophenylpropyl)-L-alanyl-L-proline.

EXAMPLE 71

N-[1-Ethoxycarbonyl-2-(3-indolyl)ethyl]-L-alanyl-L-proline

In the manner described in Example 26, the ethyl ester of indole-3-pyruvic acid is condensed with L-alanyl-L-proline in 1:1 ethanol:water solution by means of sodium cyanoborohydride. Isolation on Dowex 50 as described affords the mixture of isomers of N-[1-ethoxycarbonyl-2-(3-indolyl)ethyl]-L-alanyl-L-proline. The nmr spectrum showed absorbance at 7.0δ (5H), 4.2δ (5H), 3.4δ (2H), 2.9δ (2H), 1.9δ (6H) and 1.2δ (6H).

EXAMPLE 72

N-(1-Ethoxycarbonyl-2-p-aminomethylphenylethyl)-L-alanyl-L-proline

Condense ethyl 2-oxo-3-p-cyanophenylpropanoate (prepared by coupling p-cyanobenzyl bromide with ethyl 1,3-dithiane-2-carboxylate and subsequent oxidative hydrolysis in the manner described by Eliel and Hartmann, *J. Org. Chem.*, 37, 505 (1972)) and L-alanyl-L-proline and purify the product by the method described in Example 1. Hydrogenate the resulting mixture of isomers of N-(1-ethoxycarbonyl-2-p-cyanophenylethyl)-L-alanyl-L-proline in ethanol solution containing hydrogen chloride and palladium on carbon catalyst. Distill off the solvent and excess HCl in vacuo, flush with ethanol, and concentrate to dryness to obtain the hydrochlorides of the mixtures of diastereoisomers of the desired compound.

EXAMPLE 73

N-(1-Carboxy-2-p-aminomethylphenylethyl)-L-alanyl-L-proline

Treat a sample of N-(1-ethoxycarbonyl-2-p-cyanophenylethyl)-L-alanyl-L-proline, prepared in Example 72, with one equivalent of sodium hydroxide in a mixture of methanol and water as solvent at room temperature overnight. Distill off the solvents in vacuo to obtain the sodium salts of the mixture of isomers of N-(1-carboxy-2-cyanophenylethyl)-L-alanyl-L-proline. Hydrogenate this mixture in ethanolic hydrogen chloride solution and work up as described in Example 72 to obtain the hydrochlorides of the mixture of diastereoisomers of the desired compound.

EXAMPLE 74

N-(1-Ethoxycarbonyl-2(S)-amino-3-phenylpropyl)-D,L-alanyl-L-proline

To a mixture of N-phthaloyl-L-2-amino-3-phenylpropionaldehyde (Peterson et al., *J. Am. Chem. Soc.*, 79, 1389 (1957)), (2.18 g) and potassium metabisulfite (0.87 g) in water:methanol 1:1, add sodium cyanide (0.55 g) with vigorous stirring. Stir for 90 minutes, dilute with ethyl acetate and filter. Wash the organic layer with water and dry over magnesium sulfate. Remove the solvent in vacuo to obtain N-phthaloyl-3-amino-4-phenyl-2-hydroxybutyronitrile, tlc in ethyl acetate:hexane 1:1, $r_f$0.5.

Allow a solution of this material in anhydrous ethanol which is saturated with ammonia to stand for 6 days at room temperature. Remove the solvent, take up the residue in dioxane:conc. hydrochloric acid (1:1), warm to 70° and hold at that temperature for 20 hours. Evaporate the solution to dryness, slurry the residue with warm water, filter, and purify on a strong acid cation exchange resin in the usual manner to obtain (2R,S;3S)-2-amino-4-phenyl-3-phthaloylaminobutanoic acid. Dissolve the acid in anhydrous ethanol, pass in anhydrous hydrogen chloride until saturated, and hold for 16 hours at room temperature. Remove the solvent in vacuo to obtain the ethyl ester hydrochloride of the amino acid.

Condense this ethyl 2-amino-4-phenyl-3-phthalylamino butanoate with pyruvoyl-L-proline by means of sodium cyanoborohydride in the manner described in Example 16 to obtain N-(1-ethoxycarbonyl-3-phenyl-2-phthaloylaminopropyl)-D,L-alanyl-L-proline as a mixture of isomers. Reflux this material in ethanol with one equivalent of hydrazine for 1.5 hours, cool and filter off the phthalhydrazide, and isolate the desired product from the resulting mixture by chromatographic methods to obtain N-(1-carbethoxy-2-(S)-amino-3-phenylpropyl)-D,L-alanyl-L-proline. The 300 MHz nmr spectrum had peaks at 7.3δ (5H), 3.2 and 4.4δ (3H), 2.75δ (2H), 2.0δ (4H) and 1.1δ (6H).

EXAMPLE 75

N-(1-Carboxy-2-(S)-amino-3-phenylpropyl)-D,L-alanyl-L-proline

Condense 2-amino-4-phenyl-3-(S)-3-phthaloylamino butanoic acid, prepared in Example 74, with pyruvoyl-L-proline by means of sodium cyanoborohydride in the manner described in Example 16 to obtain N-(1-carboxy-3-phenyl-2-phthaloylamino-D,L-alanyl-L-proline as a mixture of isomers. Reflux this material in ethanol with one equivalent of hydrazine for 1.5 hours, cool, filter off the phthalhydrazide, and isolate the desired product by chromatographic methods to obtain the title compound. Thin layer chromatography on silica gel eluted with EtOAc:5 pyridine:1 HOAC:3 H$_2$O gave a spot with R$_f$0.15.

EXAMPLE 76

N-(1-Carboxy-2-(S)-benzoylamino-3-phenylpropyl)-D,L-alanyl-L-proline

Allow a solution of N-phthaloyl-3-amino-4-phenyl-2-hydroxy butyronitrile (prepared in Example 74) in ethanol saturated with anhydrous ammonia to stand for 3 days at room temperature. Remove the solvent in vacuo and reflux the residue for 6 hours in concentrated hydrochloric acid. Evaporate to dryness, and purify the residue on a column of Dowex-50 (H+) ion-exchange resin, eluting in sequence with water-methanol 10:1, water-pyridine 50:1, and finally 0.5 M ammonium hydroxide solution. Isolate the desired 2,3-diamino-4-phenyl propionic acid from this last eluant by concentration to dryness. Prepare a solution of the copper complex of this amino acid and benzoylate the 3-amino group in situ with benzoyl chloride under basic conditions, all by the method described by R. Roeske et al., *J. Am. Chem. Soc.*, 78, 5883 (1956). Cleave the copper complex with hydrogen sulfide and work up as described therein to obtain the 2-amino-3-(S)-benzoylamino-4-phenyl butyric acid. Condense this intermediate with pyruvoyl-2-proline by means of sodium cyanoborohydride in the manner described in Example 16 to obtain the desired N-(1-carboxy-2-(S)-benzoylamino-3-phenylpropyl)-D,L-alanyl-L-proline as a mixture of isomers which may be separated by chromatographic methods if desired. Mass spectral analysis showed a peak at 596 m/e for the disilyated molecular ion minus 15. The nmr spectrum showed absorbance for two phenyls at 7.0–7.5δ and diastereomeric methyls at 1.1δ.

EXAMPLE 77

N-(1-Ethoxycarbonyl-2-(S)-benzoylamino-3-phenylpropyl)-D,L-alanyl-L-proline

Treating 2-amino-3-benzoylamino-4-phenylbutyric acid (prepared in Example 76) with a saturated solution of hydrogen chloride in absolute ethanol for 4 hours, then stripping off the solvent in vacuo, one can obtain ethyl 2-amino-3-benzoylamino-4-phenyl butyrate hydrochloride. Condensing this intermediate with pyruvoyl-L-proline by means of sodium cyanoborohydride in the manner described in Example 16 and isolating as described therein, one can obtain the title compound.

EXAMPLE 78

N-[2-Amino-1-carboxy-4-methylpentyl]-D,L-alanyl-L-proline

A solution of 0.731 g. of trans-3-amino-4-(2-methylpropyl)-2-azetidinone (prepared by chlorosulfonyl isocyanate addition to 4-methyl-1-pentene. The obtained β-lactam is protected as the t-butyldimethylsilyl derivative and then treated with lithium diisopropylamide followed by tosyl azide and chlorotrimethylsilane. Acidic work up and silica gel chromatography affords the trans-3-azido-4-(2-methylpropyl)-2-azetidinone which is hydrogenated (10% Pd/C ethanol) to the amino derivative) and 4.58 g. of benzyl pyruvate in 20 ml of absolute ethanol containing 10 g of powdered 4 A molecular sieves is treated dropwise with a solution of sodium cyanoborohydride (0.65 g) in 8 ml of absolute ethanol and stirred until reaction is complete. The reaction mixture is filtered and the filtrate concentrated. The residue is dissolved in 50 ml of water and acidified with 1 N HCl to pH=3. The mixture is readjusted to pH=9.5 with 10% sodium carbonate solution. The aqueous solution is saturated with sodium chloride and extracted with ethyl acetate (5×40 ml). The combined organic layers are dried (sodium sulfate) and concentrated to give an oil (4.94 g.). Chromatography on silica gel (ethyl acetate) affords 1.11 g of product. NMR and mass spectrogram are consistent with the structure N-[trans-4-(2-methylpropyl)-2-oxo-3-azetidinyl]-D,L-alanine benzyl ester. Debenzylation is accomplished by catalytic hydrogenation (10% Pd/C, 2:1 ethanol:water). A cold solution (0°) of the acid (428 mg) and L-proline t-butyl ester (377 mg) in 5 ml of dimethylformamide is treated with a solution of diphenylphosphoryl azide (605 mg) in 5 ml of dimethylformamide and then with a solution of triethylamine (223 mg in 5 ml of dimethylformamide) over 20 minutes. After three hours the ice bath is removed and the reaction mixture permitted to stir at ambient temperature overnight. Ethyl acetate (100 ml) is added and the resulting solution washed with water (2×40 ml), 5% sodium carbonate solution (3×30 ml), and water (1×50 ml) before drying with sodium sulfate. Concentration affords an oil, 0.78 g, whose nmr and mass spectra are consistent with the N-[trans-4-(2-methylpropyl)-2-oxo-3-azetidinyl]-D,L-alanyl-L-proline-t-butyl ester structure. The crude product is dissolved in 25 ml of trifluoroacetic acid (at 0°). The reaction mixture is stirred at 0° for twenty minutes and then at room temperature for 2½ hrs. The reaction mixture is concentrated to dryness and the residue treated with 1 N NaOH (30 ml) for 4.5 hr. at room temperature. The basic mixture is slowly added to a strong acid ion-exchange resin and the product recovered with 2% pyridine in water. Freeze-drying affords 0.30 g of N-[2-amino-1-carboxy-4-methylpentyl]-D,L-alanyl-L-proline which consists of four diastereomers (S,S,S,S,; S,S,R,S; R,R,R,S; R,R,S,S) separable by chromatography. Nmr and mass spectrogram are consistent with structure. The nmr spectrum shows multiplets centered at 4.5, 3.85, 2.3, 1.79, and 1.16 ppm. The mass spectrogram shows a peak at 458 (disilylated molecular ion −15).

EXAMPLE 79

N-(2-Amino-1-ethoxycarbonyl-4-methylpentyl)-D,L-alanyl-L-proline

An intermediate in Example 78, N-(trans-4-(2-methylpropyl)-2-oxo-3-azetidinyl]-D,L-alanine (125 mg) can be condensed with L-proline benzyl ester hydrochloride (167 mg) in the presence of diphenylphosphorylazide (191 mg) and triethylamine (140 mg) in dimethylformamide solution to yield 217 mg of N-[trans-4-(2-methylpropyl)-2-oxo-3-azetidionyl]-D,L-alanyl-L-proline benzyl ester. The benzyl protecting group can be removed by hydrogenolysis and the β-lactam can be opened with anhydrous sodium ethoxide in ethanol so that one can obtain N-(2-amino-1-ethoxycarbonyl-4-methyl-pentyl)-D,L-alanyl-L-proline.

EXAMPLE 80

N-(2-Benzamido-1-carboxy-4-methylpentyl)-D,L-alanyl-L-proline

A solution of N-(2-amino-1-carboxy-4-methylpentyl)-D,L-alanyl-L-proline (prepared as described in Example 78) in aqueous alkali is treated with benzoyl chloride to yield N-(2-benzamido-1-carboxy-4-methylpentyl)-D,L-alanyl-L-proline. The mass spectrum of disilylated material had peaks at 562 (M+−15), 460,389 (base peak), 364,242 and 174 m/e.

EXAMPLE 81

N-(2-Benzamido-1-ethoxycarbonyl-4-methylpentyl)-D,L-alanyl-L-proline

By treating a solution of N-(2-amino-1-ethoxycarbonyl-4-methylpentyl)-D,L-alanyl-L-proline (prepared as described in Example 79) in organic solvent with benzoyl chloride, one can obtain N-(2-benzamido-1-ethoxycarbonyl-4-methylpentyl)-D,L-alanyl-L-proline.

EXAMPLE 82

N-α-[1-Ethoxycarbonyl-3-phenylpropyl]-L-arginyl-L-proline

In the manner described in Example 37, condense N-α-t-Boc-N-ω-nitro-L-arginine N-hydroxy succinimide ester with L-proline in dioxane-water, remove the N-α-t-Boc protecting group with trifluoracetic acid, and isolate the dipeptide as described. Couple with ethyl 2-oxo-4-phenylbutyrate as described in Example 26 and isolate as described to obtain material with the ω-nitrogen of the arginine still protected by the nitro group. Remove this protection by catalytic hydrogenation in ethanol-water-acetic acid over palladium on carbon catalyst at room temperature and 40 lbs. hydrogen pressure. Filter off the catalyst and distill off the solvents in vacuo to obtain the mixture of isomers of N-α-(1-ethoxycarbonyl-3-phenylpropyl)-L-arginyl-L-proline.

EXAMPLE 83

N-α-(1-Carboxy-3-phenylpropyl)-D,L-homolysyl-L-proline

The condensation of N-ω-benzyloxy-carbonyl-N-α-3°-butoxycarbonyl-D,L-homolysine (prepared from homolysine via the copper complex) with L-proline 3° butyl ester can be effected by means of diphenyl phosphorylazide. The 3° butyl groups can then be removed with trifluoroacetic acid and the product, N-ω-benzyloxycarbonyl-D,L-homolysyl-L-proline can be reacted with 2-oxo-4-phenylbutyric acid and NaBH3CN. The condensation product can be de-benzylated by catalytic hydrogenation so that one can obtain N-α-(1-carboxy-3-phenylpropyl)-D,L-homolysyl-L-proline.

EXAMPLE 84

N-α-(1-Ethoxycarbonyl-3-phenylpropyl)-D,L-homolysyl-L-proline

The intermediate described in Example 83, N-ω-benzyloxycarbonyl-D,L-homolysyl-L-proline, can be reacted with ethyl 2-oxo-4-phenylbutyrate and NaBH3CN. The condensation product can then be hydrogenated over palladium on carbon so that one can then obtain N-α-(1-ethoxycarbonyl-3-phenylpropyl)-D,L-homolysyl-L-proline.

EXAMPLE 85

N-α-(1-Carboxy-3-Phenylpropyl)-β-amino-D,L-alanyl-L-proline

Under basic conditions, DL-α,β-diaminopropionic acid is reacted with excess benzyloxycarbonyl chloride to yield upon acidification D,L-α,β-bis(benzyloxycarbonylamino)-propionic acid (mp=123.5°–124° C. ). Phosphorous pentachloride is added to a chloroform solution containing the di-Cbz product to yield on workup D,L-4-(benzyloxycarbonylaminomethyl)-oxazolidin-2,5-dione. A solution of L-proline t-butyl ester in methylene chloride is added to the N-carboxy-anhydride in tetrahydrofuran at −60° C. After overnight freezer storage, the mixture is stripped to dryness affording crude product. Trifluoroacetic acid effectively cleaves the t-butyl ester in 2 hours at room temperature resulting in a gross mixture of L-proline and β-benzyloxycarbonylamino-D,L-alanyl-L-proline. Gel filtration chromatography (LH-20) results in pure dipeptide. 2-Oxo-4-phenylbutyric acid and benzyloxycarbonylamino-D,L-alanyl-L-proline are condensed in the presence of sodium cyanoborohydride. Removal of the protecting group from the resulting product yields N-(1-carboxy-3-phenylpropyl)-β-amino-D,L-alanyl-L-proline. The nmr in D$_2$O showed aromatic protons at 7.4δ, methine protons at 4.2δ and multiplets at 3.7, 3.2, 2.9 and 2.1δ.

EXAMPLE 86

N-α-(1-Ethoxycarbonyl-3-phenylpropyl)-β-amino-D,L-alanyl-L-proline

A solution of β-benzyloxycarbonylamino-D,L-alanyl-L-proline (prepared as described in Example 85) and ethyl 2-oxo-4-phenylbutyrate can be condensed in ethanol solution with NaBH$_3$CN. The protecting group can be removed from the product by catalytic hydrogenation so that one obtains N-α-(1-ethoxy-carbonyl-3-phenylpropyl)-β-amino-D,L-alanyl-L-proline.

EXAMPLE 87

N-(1(S)-Ethoxycarbonyl-3-phenylpropyl)-D,L-p-aminomethylphenylalanyl-L-proline Hydrolyze ethyl 2-oxo-3-p-cyanophenylpropionate, prepared in Example 72, by stirring in 5% sodium hydroxide at room temperature overnight, washing the reaction mixture with ether, acidifying the aqueous layer to pH 2 with conc. HCl, extracting the product into a mixture of ether and ethyl acetate, and removing the solvent to obtain 2-oxo-3-p-cyanophenylpropionic acid. Reductively couple the acid with the ethyl ester of L-homophenylalanine in the presence of sodium cyanoborohydride in the manner described in Example 13 and purify as described in that Example to obtain the mixture of diastereoisomers of N-(1(S)-ethoxycarbonyl-3-phenylpropyl)-D,L-p-cyanophenylalanine. Condense this with benzyl L-prolinate hydrochloride in dimethylformamide by the use of the diphenylphosphoryl azide reagent in the manner described in Example 13 to obtain the mixture of diastereoisomers of N-(1-(S)-carbethoxy-3-phenylpropyl)-D,L-p-cyanophenylalanyl-L-proline benzyl ester. Hydrogenate this intermediate in ethanol containing hydrogen chloride over palladium on carbon catalyst as described in Example 72 and work up as outlined there to obtain the desired product as a mixture of diastereoisomers.

EXAMPLE 88

N-α-(1(S)-Carboxy-3-phenylpropyl)-D,L-p-aminomethylphenylalanyl-L-proline

Hydrolyze the N-(1(S)-ethoxycarbonyl-3-phenylpropyl)-D,L-p-cyanophenylalanyl-L-proline benzyl ester prepared in Example 87 by treating with two equivalents of sodium hydroxide in a mixture of methanol and water at room temperature overnight. Strip the solvent from the reaction mixture in vacuo and hydrogenate the residue in ethanolic hydrogen chloride as in Example 72 and work up as described there to obtain the mixture of diastereoisomers of the desired compound.

EXAMPLE 89

N-α-(1-Ethoxycarbonyl-3-phenylpropyl)-N-acetyl-L-lysyl-L-proline

In the manner described in Example 26, couple ethyl 2-oxo-4-phenylbutyrate with N-ε-acetyl-L-lysyl-L-proline in ethanol-water solution in the presence of sodium cyanoborohydride. Isolate on Dowex-50 as described and freeze-dry the product-rich cuts to obtain the mixture of isomers of N-(1-ethoxycarbonyl-3-phenylpropyl)-N-ε-acetyl-L-lysyl-L-proline. The mass spectrum of the trisilylated material had peaks at 663(M+), 648(M+ −15) and 546 m/e.

EXAMPLE 90

N-α-(1-Ethoxycarbonyl-3-phenylpropyl)-L-histidyl-L-proline

In the manner described in Example 26, couple ethyl 2-oxo-4-phenylbutyrate with L-histidyl-L-proline in the presence of sodium cyanoborohydride. Purify as described to obtain the mixture of diastereoisomers of N-α-(1-ethoxycarbonyl-3-phenylpropyl)-L-histidyl-L-proline.

EXAMPLE 91

A.

N-α-(Ethoxycarbonyl-3-α-naphthylpropyl)-L-lysyl-L-proline

Ethyl 4-α-naphthyl-2-oxobutyrate (prepared by alkylation of ethyl 1,3-dithiane-2-carboxylate with 2-α-naphthylethyl bromide and subsequent conversion to the ketone with N-bromosuccinimide in aqueous acetone) can be condensed with ε-3° butoxycarbonyl-L-lysyl-L-proline in ethanol in the presence of NaBH$_3$CN and molecular sieves. The product can then be absorbed on strong acid ion-exchange resin and eluted with 2% pyridine in water. Removal of the t-Boc group can be completed by treatment with 4.0 N HCl in ethyl acetate so that one can obtain N-α-(1-ethoxycarbonyl-3-α-naphthylpropyl)-L-lysyl-L-proline.

B.

N-α-(1-Carboxy-3-α-naphthylpropyl)-L-lysyl-L-proline

A slurry of 4-α-naphthyl-2-oxobutyric acid (prepared from the ester by hydrolysis) in water is adjusted to pH 7 with dilute NaOH and freeze-dried. The residue is treated with ε−3°-butoxycarbonyl-L-lysyl-L-proline as described in Example 91A to yield N-α-(1-carboxy-3-α-naphthylpropyl)-L-lysyl-L-proline.

EXAMPLE 92

N-α-(1(S)Carboxy-3-p-chlorophenylpropyl)-L-lysyl-L-proline

A solution of ε−3°-butoxycarbonyl-L-lysyl-L-proline (0.36 g) and 4-p-chlorophenyl-2-oxobutyric acid (1.1 g) in 5 ml of water is adjusted to pH 7 with dilute NaOH and treated with 0.07 g of NaBH$_3$CN in 1 ml of water over the course of several hours. After stirring overnight at room temperature the product is absorbed on strong acid ion-exchange resin and eluted with 2% pyridine in water to yield 0.058 g of product. Nmr indicates the t-Boc protecting group is not completely removed. The product is treated with 4.5 N HCl in ethyl acetate, followed by ion-exchange isolation, to yield 0.048 g of N-α-(1-carboxy-3-p-chlorophenylpropyl)-L-lysyl-L-proline. Nmr and mass spectrum are consistent with structure. A peak at 584 is found for the silylated molecular ion. Chromatography affords the desired isomer.

EXAMPLE 93

N-α-(1-Ethoxycarbonyl-3-p-chlorophenyl)-L-lysyl-L-proline

By condensing ethyl 4-p-chlorophenyl-2-oxobutyrate and ε−3°-butoxycarbonyl-L-lysyl-L-proline in ethanol solution with excess NaBH$_3$CN and isolating product as described in Example 92, one can obtain N-α-(1-ethoxycarbonyl-3-p-chlorophenylpropyl)-L-lysyl-L-proline.

EXAMPLE 94

N-α-[1-Carboxy-3-(3,4-dichlorophenyl)-propyl]-L-lysyl-L-proline

A solution of 4-(3,4-dichlorophenyl)-2-oxobutyric acid (prepared from the dichlorodihydrocinnamate ester by condensation with ethyl oxalate and subsequent acid catalyzed hydrolysis and partial decarboxylation) in water is treated as described in Example 92 to yield N-α-[1-carboxy-3-(3,4-dichlorophenyl)-propyl]-L-lysyl-L-proline. The nmr spectrum in D$_2$O showed aromatic hydrogen at 7.30δ, a broad singlet at 4.35δ and broad multiplets at 3.53, 3.00, 2.68, 1.98 and 1.65δ. The mass spectrum showed a parent peak at 455 m/e which corresponded to loss of H$_2$O from the desired structure upon injection. A large M+2 (457 m/e) isotope contribution confirmed the presence of 2 Cl.

EXAMPLE 95

N-α-[1(S)-Carboxy-3-(3-indolyl)propyl]-L-lysyl-L-proline

Prepare 2-oxo-4-(3-indolyl)-butyric acid from homotryptophane by the method described by Weygand et al., Ann. 658, 128 (1962). Condense this with ε-t-Boc-L-lysyl-L-proline in the presence of sodium cyanoborohydride as described in Example 54 to obtain the crude mixture of diastereoisomers of N-α-(1-carboxy-3-(3-indolyl)propyl)-N-ε-t-Boc-L-lysyl-L-proline. The mass spectrum of tetrasilylated material had peaks at 732(M+), 717(M+−15), 615, 660, and 645 m/e. Deprotect the lysine side chain by treatment with 4 N hydrogen chloride in ethyl acetate and purify on a strong acid ion-exchange resin as described in that Example to obtain the desired product. Chromatography affords the desired isomer.

EXAMPLE 96

N-α-(6-Amino-1-carboxyethyl)-L-lysyl-L-proline

Benzyl 2-oxo-7-phthalimidoheptanoate and ε−3°-butoxycarbonyl-L-lylyl-L-proline can be condensed with excess NaBH$_3$CN in ethanol solution to yield N-α-(1-benzyloxycarbonyl-6-phthalimidohexyl)-N-ε−3° butoxycarbonyl-L-lysyl-L-proline. One can then remove the benzyl group by hydrogenation over Pd, remove the t-boc group with 4.5 N HCl in ethyl acetate, and remove the phthalimido group by treatment with hydrazine to obtain N-α-(6-amino-1-carboxyhexyl)-L-lysyl-L-proline.

EXAMPLE 97

N-α-(6-Amino-1-benzyloxycarbonylhexyl)-L-lysyl-L-proline

By treating N-α-(1-benzyloxycarbonyl-6-phthalimidohexyl)-N-ε−3° butoxycarbonyl-L-lysyl-L-proline (prepared as described in Example 96) with 4.0 N HCl in ethyl acetate and then with an equivalent of hydrazine in refluxing ethanol, one can obtain a mixture from which N-α-(6-amino-1-benzyloxycarbonylhexyl)-L-lysyl-L-proline can be isolated.

EXAMPLE 98

N-α-(5-Amino-1(S)-carboxypentyl)-L-lysyl-L-proline

Benzyl 2-oxo-6-phthalimidohexanoate is treated as described in Example 96 to give N-α-(5-amino-1-carboxylpentyl)-L-lysyl-L-proline. Chromatography affords the desired isomer. The mass spectrum indicated the molecular ion for the disilylated species at 516 m/e, the M+−15 ion at 501 m/e and a peak at 399 m/e corresponding to a loss of silylated carboxyl.

EXAMPLE 99

N-α-(5-Amino-1-benzyloxycarbonylpentyl)-L-lysyl-L-proline

Benzyl 2-oxo-6-phthalimidohexanoate can be treated as described in Example 96 except that the debenzylation with hydrogen over palladium can be omitted. From the mixture of products one can isolate the desired N-α-(5-amino-1-benzyloxycarbonyl-pentyl)-L-lysyl-L-proline.

EXAMPLE 100

A. N-α-(1-Carboxy-2-phenoxyethyl)-L-lysyl-L-proline

Phenoxy pyruvic acid (0.9 g) is dissolved in water, the pH adjusted to 7 with dilute NaOH and the solution freeze dried. The residue is dissolved in 10 ml of ethanol and treated with ε−3°-butoxycarbonyl-L-lysyl-L-proline (0.36 g) and powdered No. 4A molecular sieves (3.0 g). Sodium cyanoborohydride (0.18 g in 3.5 ml of ethanol) is added portionwise and the reaction stirred at room temperature until the reaction is complete. The product is isolated by absorption on strong acid ion-exchange resin and elution with 2% pyridine in water, followed by freeze-drying to yield 0.25 g. of deprotected product, N-α-(1-carboxy-2-phenoxyethyl)-L-lysyl-L-proline. The nmr and mass spectra are consistent with structure.

B.
N-α-(1-Ethoxycarbonyl-2-phenoxyethyl)-L-lysyl-L-proline.

Ethyl phenoxypyruvate treated with ε—3°-butoxycarbonyl-L-lysyl-L-proline as described in Example 100A gives N-α-(1-ethoxycarbonyl-2-phenoxyethyl)-L-lysyl-L-proline. The nmr spectrum showed phenyl absorption centered at 7.3δ, and broad peaks at 4.6, 4.4, 4.2, 3.7, 3.2 and 1.9δ.

EXAMPLE 101

A.
N-α-(1(S)-Carboxy-2-Phenylthioethyl)-L-lysyl-L-proline

Phenylthiopyruvic acid is treated with ε—3°-butoxycarbonyl-L-lysyl-L-proline as described in Example 100 to yield N-α-(1-carboxy-2-phenylthioethyl)-L-lysyl-L-proline. The mass spectrum shows a silylated molecular ion at 567 m/e. Chromatography affords the desired isomer.

B.
N-α-(1-Ethoxycarbonyl-2-phenylthioethyl)-L-lysyl-L-proline

Similarly, one can treat ethyl phenylthiopyruvate with ε—3°-butoxycarbonyl-L-lysyl-L-proline as described in Example 100A to obtain N-α-(1-ethoxycarbonyl-2-phenylthioethyl)-L-lysyl-L-proline.

EXAMPLE 102

N-α-(1-Carboxy-2(S)-amino-3-phenylpropyl)-D,L-Lysyl-L-proline

One can condense ethyl 2-amino-4-phenyl-3-phthalimidobutanoate with 2-oxo-6-phthalimidohexanoic acid (prepared by alkylation of benzyl 1,3-dithiane-2-carboxylate with phthalimidobutylbromide followed by oxidation and hydrolysis) in the presence of sodium cyanoborohydride by the procedure described in Example 13. The resulting intermediate can then be coupled with L-proline benzyl ester hydrochloride by means of diphenylphosphoryl azide as described in that Example to obtain a mixture of isomers of N-α-(1-ethoxycarbonyl-2(S)-phthalimido-3-phenylpropyl)-N-ε-phthaloyl-D,L-lysyl-L-proline benzyl ester, purified by column chromatography. One can then treat with two equivalents of sodium hydroxide in ethanol-water solution for four hours at room temperature, neutralize to pH 4 with conc. hydrochloric acid, distill off the ethanol in vacuo, extract the product into ethyl acetate, and remove the solvent in vacuo. This residue can then be refluxed in ethanol containing 2 equivalents of hydrazine for 1.5 hours and isolated, as described in Example 74, so that one can obtain the desired compound.

EXAMPLE 103

N-α-(1-Carboxy-2-(S)-benzoylamino-3-phenylpropyl)-D,L-lysyl-L-proline

One can condense ethyl 2-amino-3-benzoylamino-4-phenylbutanoate (prepared in Example 77) with 2-oxo-6-phthalimido hexanoic acid in the presence of sodium cyanoborohydride by the method described in Example 13. The resulting N-α-(1-carbethoxy-2-(S)-benzoylamino-3-phenylpropyl)-N-ε-phthaloyl-D,L-lysine can then be coupled with L-proline benzyl ester hydrochloride by means of diphenylphosphoryl azide as described in the same Example to obtain a mixture of isomers of N-α-(1-carbethoxy-2-(S)-benzoylamino-3-phenylpropyl)-N-ε-phthaloyl-D,L-lysyl-L-proline benzyl ester, purified by chromatography. Treating with two equivalents of sodium hydroxide in ethanol-water solution for four hours at room temperature and working up as described in Example 102, one can obtain N-α-(1-carboxy-2-(S)-benzoylamino-3-phenylpropyl)-N-ε-phthaloyl-D,L-lysyl-L-proline. By refluxing this in ethanol for 1.5 hours in the presence of one equivalent of hydrazine and isolating as described in Example 74, one can obtain the desired compound as a mixture of isomers.

EXAMPLE 104

N-α-(2-amino-1-carboxy-4-methylpentyl)-D,L-lysyl-L-proline

An ethanol solution of trans-3-amino-4-(2-methylpropyl)-2-azetidinone (as prepared in Example 78) can be reductively coupled with benzyl 2-oxo-6-phthalimidohexanoate by the use of NaBH₃CN and molecular sieves. The product, N-α-[4-(2-methylpropyl)-2-oxo-3-azetidinyl]-N-ε-phthaloyl-D,L-lysine benzyl ester, can then be debenzylated by hydrogenation over palladium. The free acid and proline benzyl ester can be coupled with diphenylphosphoryl azide and the product subsequently de-benzylated as above to obtain N-α-[4-(2-methylpropyl)-2-oxo-3-azetidin-yl]-N-ε-phthaloyl-D,L-lysyl-L-proline. The phthaloyl group can be removed at room temperature in ethanol solution with one molar equivalent of hydrazine to obtain N-α-[4-(2-methylpropyl)-2-oxo-3-azetidinyl]-D,L-lysyl-L-proline. By hydrolysis with dilute sodium hydroxide, by β-lactam ring opening, one can obtain N-α-(2-amino-1-carboxy-4-methylpentyl)-D,L-lysyl-L-proline.

EXAMPLE 105

N-α-(2-Benzamido-1-carboxy-4-methylpentyl)-D,L-lysyl-L-proline

N-α-[4-(2-methylpropyl)-2-oxo-3-azetidinyl]-N-ε-3°-butoxycarbonyl-D,L-lysine benzyl ester can be prepared from trans-3-amino-4-(2-methylpropyl)-2-azetidinone (Example 78) and benzyl ε-3°-butoxy carbonylamino-2-oxohexanoate. The benzyl group can be removed by hydrogenation and the product coupled with L-proline benzyl ester. The product, N-α-[4-(2-methylpropyl)-2-oxo-3-azetidinyl]-N-ε-3°-butoxycarbonyl-D,L-lysyl-L-proline benzyl ester, can then be debenzylated with hydrogen and the β-lactam hydrolyzed with dilute base to obtain N-α-(2-amino-1-carboxy-4-methylpentyl)-N-ε-3°-butoxycarbonyl-D,L-lysyl-L-proline. After benzoylation with benzoyl chloride in organic solvent, the t-Boc protecting group can be removed with trifluoroacetic acid so that one can obtain N-α-(2-benzamido-1-carboxy-4-methylpentyl)-D,L-lysyl-L-proline.

EXAMPLE 106

N-α-(1(S)-Carboxy-3-p-chlorophenylpropyl)-L-lysyl-trans-4-methoxy-L-proline

Couple methyl-trans-4-methoxy-L-prolinate hydrochloride with N-α-t-Boc-N-ε-Cbz-L-lysine using dicyclohexylcarbodiimide and triethylamine in methylene chloride, as described in Example 20. Purify by chromatography, hydrolyze the ester, and remove the t-Boc protecting group as described in that Example. Reductively couple this ε-Cbz-L-lysyl-L-4α-methoxyproline with 2-oxo-4-p-chlorphenyl butyric acid (prepared from p-chlorhydrocinnamic acid ethyl ester by base catalyzed condensation with diethyl oxalate, followed by decarboxylation in anhydrous hydrogen chloride in acetic acid) in the presence of sodium cyanoborohydride and workup as described in Example 24 to obtain the mixture of isomers of N-α-(1-carboxy-3-p-chlorophenylpropyl)-N-ε-Cbz-L-lysyl-trans-4-methoxy-L-proline. Remove the benzyloxycarbonyl protecting group by catalytic hydrogenation over palladium on carbon catalyst in the usual manner. Chromatography affords the desired isomer. The mass spectrum had peaks at 584(M+ +1), 568(M+ −15), 466, 397, 366 and 352 (base peak) for the disilylated material.

EXAMPLE 107

N-α-(1-Carboxy-3-p-chlorophenylpropyl)-L-lysyl-L-4-thiazolidine carboxylic acid One can couple N-α-t-Boc-N-ε-Cbz-L-lysine with L-thiazolidine-4-carboxylic acid benzyl ester hydrochloride, purify by chromatography, hydrolyze the ester, and remove the t-Boc protecting group, all by the methods described in Example 20. By reductively coupling this with 2-oxo-4-p-chlorphenylbutyric acid as described in that Example, one can obtain the mixture of isomers of N-α-(1-carboxy-3-p-chlorphenylpropyl)-N-ε-Cbz-L-lysyl-L-4-thiazolidine carboxylic acid. By removing the benzyloxycarbonyl protecting group by treatment with hydrogen bromide in acetic acid at room temperature in the manner standard in peptide chemistry, stripping off the solvent in vacuo, flushing with water and finally freeze-drying, one can obtain the desired product.

EXAMPLE 108

N-α-(1-Carboxy-3-p-chlorphenylpropyl)-L-lysyl-D,L-trans-5-methylthiazolidine-4-carboxylic acid One can couple 3.7 g of trans-5-methylthiazolidine-4-carboxylic acid ethyl ester hydrochloride (prepared from α-bromocrotonic acid and thioacetamide, acid hydrolysis to β-methylcysteine, and subsequent reaction with formaldehyde, following the method employed by R. F. Nutt et al, Abstracts of the 6th American Peptide Symposium, Washington, D.C. (1979), I-16, p. 95) with 7.4 g. of N-α-t-Boc-N-ε-Cbz-L-lysine, employing 2.8 ml of triethylamine and 4.5 g of dicyclohexylcarbodiimide in methylene chloride as described in Example 20. By reductively coupling this intermediate with 2-oxo-4-p-chlorphenylbutyric acid employing sodium cyanoborohydride and then removing the benzyloxycarbonyl protecting group as described in Example 107, one can obtain N-α-(1-carboxy-3-p-chlorphenylpropyl)-L-lysyl-D,L-trans-5-methylthiazolidine-4-carboxylic acid as a mixture of isomers.

EXAMPLE 109

N-α-(1-Carboxy-3-p-chlorphenylpropyl)-L-lysyl-L-3,4-dehydroproline

Condense L-3,4-dehydroproline ethyl ester hydrochloride with N-α-t-Boc-N-ε-Cbz-L-lysine, remove the t-Boc group with 4 M HCl in ethyl acetate, then reductively couple the intermediate with 2-oxo-4-p-chlorphenylbutyric acid; remove the protecting group with HBr in acetic acid and work up, all by the method described in Example 107 to obtain the mixture of isomers of N-α-(1-carboxy-3-p-chlorophenylpropyl)-L-lysyl-L-3,4-dehydroproline.

EXAMPLE 110

N-(1-Carboxy-4-methylpentyl)-L-alanyl-L-proline

A solution of 5-methyl-2-oxohexanoic acid (1.44 g) and L-alanyl-L-proline (0.37 g) in 5 ml of water is adjusted to pH 7 and treated with NaBH₃CN (0.31 g). After stirring at room temperature for five days the reaction product is absorbed on strong acid ion-exchange resin and eluted with 2% pyridine in water to yield 0.6 g of freeze-dried solid. A portion (0.2 g) is purified by chromatography on an LH 20 column to give 0.18 g of N-(1-carboxy-4-methylpentyl)-L-alanyl-L-proline. The nmr and mass spectrum are in accord with the assigned structure. The diastereomers may be isolated by chromatography. Peaks were observed in the mass spectrum of the disilylated material at 458(M+), 443 (M+ −15), 341, 301 and 244 m/e (base peak).

EXAMPLE 111

N-(1(S)-Ethoxycarbonyl-4-methylpentyl)-L-alanyl-L-proline

Ethyl 5-methyl-2-oxohexanoate (3.44 ) and L-alanyl-L-proline (0.74 g) is stirred in 15 ml of ethanol with 6 of powdered 4 A molecular sieves. Sodium cyanoborohydride (0.23 g) in ethanol is added dropwise over the course of several hours. The ethanol is then removed under vacuum, the product is absorbed on strong acid ion-exchange resin and eluted with 2% pyridine in water to yield 1.08 g. of N-(1-ethoxycarbonyl-4-methylpentyl)-L-alanyl-L-proline. A portion is purified by LH-20 chromatography for spectral analysis. The nmr is in accord with structure. The mass spectrum shows a peak at 414 (silylated molecular ion −15). Chromatography affords the desired isomer.

EXAMPLE 112

N-(1-Carboxy-3-p-phenoxyphenylpropyl)-L-alanyl-L-proline

A mixture of 2-oxo-4-p-phenoxyphenylbutyric acid (prepared by reaction of p-phenoxyphenyl Grignard reagent with ethylene oxide, conversion of the resultant alcohol to the bromide and condensation with ethyl 1,3-dithiane-2-carboxylate. Oxiditive cleavage of the dithiane followed by alkaline hydrolysis yields the keto acid) and L-alanyl-L-proline in water is adjusted to pH 7 with dilute alkali and treated with excess NaBH₃CN. The product, N-(1-carboxy-3-p-phenoxyphenylpropyl)-L-alanyl-L-proline is isolated by chromatography. The mass spectrum of disilylated material contained peaks at 584(M+), 569 (M+ −15), 468 and 370 m/e (base peak).

EXAMPLE 113

N-(1-Ethoxycarbonyl-3-p-phenoxyphenylpropyl)-L-alanyl-L-proline

Ethyl 2-oxo-4-p-phenoxyphenylbutyric acid (prepared as described in Example 112 except that the final alkaline hydrolysis can be omitted) can be condensed with L-alanyl-L-proline in the presence of NaBH₃CN so that one can obtain N-(1-ethoxycarbonyl-3-p-phenoxyphenylpropyl)-L-alanyl-L-proline.

EXAMPLE 114

N-(1-Carboxy-3-phenylpropyl)-L-alanyl-D,L-3,3-dimethylproline

Prepare 3,3-dimethyl-D,L-proline from 3-methyl-2-butenal by the method of Cox, *J. Chem. Soc.*, 1964, 5024, and convert to the methyl ester hydrochloride with methanolic hydrogen chloride. Couple with t-Boc-L-alanine, then condense with 2-oxo-4-phenylbutyric acid by the methods of Example 47 to obtain a mixture of isomers of the desired product.

EXAMPLE 115

A.
N-(1-Carboxy-3-phenylpropyl)-L-S-benzyl-cysteinyl-L-proline

The condensation of L-N-t-Boc-S-benzylcysteine with L-proline t-butyl ester in the presence of dicyclohexyl carbodiimide in the usual manner yields the blocked dipeptide, L-(N-t-Boc-S-benzylcysteinyl)-L-proline-t-butyl ester. The latter is treated with 4 N HCl in ethyl acetate at 0° to furnish L-(S-benzylcysteinyl)-L-proline. Treatment of this dipeptide with 2-oxo-4-phenylbutyric acid in the presence of sodium cyanoborohydride results in the formation of N-(1-carboxy-3-phenylpropyl)-L-(S-benzylcysteinyl)-L-proline as a mixture of isomers.

B.
N-(1-Carboxy-3-phenylpropyl)-L-cysteinyl-L-proline

One can treat the N-(1-carboxy-3-phenylpropyl)-L-S-benzylcysteinyl-L-proline, prepared in Part A, with sodium in liquid ammonia to obtain the desired compound.

EXAMPLE 116

N-α-(1-Carboxy-3-phenylpropyl)-L-ornithyl-L-proline

N-δ-t-BOC-L-ornithyl-L-proline and 2-oxo-4-phenylbutyric acid are condensed in the presence of sodium cyanoborohydride in the manner described in Example 54. The protecting group is removed from the product using ethyl acetate which is 4 N in hydrogen chloride gas. The crude diastereomeric HCl salt is adsorbed on strong acid ion exchange resin and eluted with an aqueous solution 2% in pyridine. The mass spectrum shows a molecular ion at 355 m/e for the product minus 36. The nmr spectrum is consistent with this structure.

EXAMPLE 117

N-α-(1(S)-Ethoxycarbonyl-3-phenylpropyl)-L-lysyl-L-proline

Ethyl 2-oxo-4-phenylbutyrate (2.58 g) and N-t-Boc-L-lysyl-L-proline (859 mg) are dissolved in absolute ethanol (50 ml) to which crushed 5 Å molecular sieves (2.0 g) are added. Upon completion of the reaction, the sieves are removed by filtration. After evaporation the filtrate residue is dissolved in water, extracted with ether and adsorbed on strong acid ion exchange resin. Elution with 2% pyridine in water gives 639 mg crude protected product, N-α-(1-ethoxycarbonyl-3-phenylpropyl)-N-ε-t-Boc-L-lysyl-L-proline. The protecting group is removed with ethyl acetate that is 4 N in hydrogen chloride gas. The resulting HCl salt is adsorbed on strong acid ion exchange resin and eluted with 2% pyridine to give 270 mg product. The mass spectrum shows a molecular ion at 678 m/e for the disilylated species plus 1. The nmr is consistent with the structure. Chromatography affords the desired isomer.

EXAMPLE 118

N-α-(1-Carboxy-3-phenylpropyl)-N-ε-N-ε-dimethyl-L-lysyl-L-proline

N-α-t-Boc-N-ε-cbz-L-lysyl-L-proline benzyl ester is reductively methylated in formaldehyde/10% Pd-C, 40 psi $H_2$. The α-t-Boc protecting group is cleaved with ethyl acetate which is 4 N in hydrochloride gas. In the manner described in Example 54, 2-oxo-4-phenylbutyric acid and N-ε-N-ε-dimethyl-L-lysyl-L-proline hydrochloride are condensed in the presence of sodium cyanoborohydride. The mass spectrum shows a molecular ion at 415 for the product minus 18. The nmr spectrum is consistent with the structure.

EXAMPLE 119

N-α-[1(S)-Carboxy-3-phenylpropyl]-L-lysyl-L-proline

N-α-(1-carboxy-3-phenylpropyl)-L-lysyl-L-proline, a mixture of diastereomers prepared as described in Example 57B is purified by gel filtration chromatrography in methanol (LH-20). The XAD-2 column prepared as described in Example 25 is equilibrated at 53° C. with 0.1 M $NH_4OH$ containing 4% acetonitrile. The isomer mixture from above (250 mg) is dissolved in 10 ml of the same solvent and added to the column. When the column is eluted with this solvent, the first isomer emerges in the volume range 320–360 ml of eluate. The second isomer emerges in the range 450–540 ml of eluate. Intermediate fractions contain a mixture of isomers. When fractions containing the first isomer are freeze-dried, 72 mg of fluffy white solid is obtained. This is the more active isomer and is the SSS configuration by analogy to the more active isomer of N-α-(1-carboxy-3-phenylpropyl)-L-alanyl-L-proline which was established by X-ray analysis to have the SSS configuration. By thin layer chromatography on silica gel in 1:1:1:1 ethylacetate/n-butanol/water/acetic acid, this solid is a single spot having an Rf value of 0.43. The 300 MHz nmr spectrum shows a triplet for the methine proton γ to the phenyl substituent at 3.40 ppm. When the fractions containing the second isomer are freeze-dried, 72 mg of white fluffy solid is obtained. This solid by thin layer chromatography is a single spot of Rf value 0.39. The 300 MHZ nmr spectrum shows the triplet for the methine proton γ to the phenyl substituent at 3.61 ppm.

EXAMPLE 120

N-α-(1-Carboxy-3-phenylpropyl)-N-ε-acetyl-L-lysyl-L-proline

In the manner described in Example 54, 2-oxo-4-phenylbutyric acid and N-ε-acetyl-L-lysyl-L-proline are condensed in the presence of sodium cyanoborohydride to yield N-α-(1-carboxy-3-phenylpropyl)-N-ε-acetyl-L-lysyl-L-proline. The nmr spectrum is consistent with structure. The mass spectrum shows a molecular ion at 663 for the trisilylated species.

EXAMPLE 121

N-α-(1-Carboxy-3-phenylpropyl)-L-arginyl-L-proline

The necessary dipeptide is prepared by DCC condensation of N-α-t-Boc-N-ω-nitro-L-arginine and L-proline benzyl ester hydrochloride salt. The α-t-Boc protecting group is removed in the usual manner with 4 N HCl in ethyl acetate and the resulting N-ω-nitro-L-arginyl-L-proline benzyl ester is condensed with 2-oxo-4-phenylbutyric acid in the manner described in Example 24.

The reaction affords fairly low yield (25–33%) of N-α-(1-carboxy-3-phenylpropyl)-N-ω-nitro-L-arginyl-L-proline benzyl ester. This compound (159 mg) is dissolved in a solution (2.5 ml) of acetic acid/water/methanol (84%, 8%, 8%) and hydrogenated at 40 psi, room temperature, over 130 mg of 10% palladium on charcoal for simultaneous removal of the ω-nitro and benzyl ester protecting groups. The catalyst is filtered off and the filtrate is evaporated to a glass (94 mg), the water soluble portion of which is freeze-dried to a fluffy white solid (90 mg). This solid is the acetate salt of the desired product and is converted to the free base by absorbing on strong acid ion exchange resin, washing with water, then eluting with 2% pyridine in water. Freeze drying of product rich cuts affords 60 mg of N-α-(1-carboxy-3-phenylpropyl)-L-arginyl-L-proline. The nmr spectrum is consistent with structure. The mass spectrum shows a molecular ion at 793 for the pentasilylated species.

EXAMPLE 122

N-(1-Carboxy-3-phenylpropyl)-L-histidyl-L-proline

In the manner described in Example 54, 2-oxo-4-phenylbutyric acid and L-histidyl-L-proline are condensed in the presence of sodium cyanoborohydride to yield N-(1-carboxy-3-phenylpropyl)-L-histidyl-L-proline. The product is purified by gel filtration chromatography in methanol (LH-20). The nmr spectrum is consistent with structure. The mass spectrum shows a molecular ion at 657 for the disilylated species.

EXAMPLE 123

N-α-[1-Carboxy-2-(3-indolyl)ethyl]-L-lysyl-L-proline

In the manner described in Example 54, indole-3-pyruvic acid is condensed with N-ε-t-Boc-L-lysyl-L-proline in the presence of sodium cyanoborohydride. The ε-t-Boc protecting group is removed from the product with 4 N HCl in ethyl acetate. The resulting hydrochloride salt is absorbed on Dowex 50 (H+) and eluted with 2% pyridine in water. Freeze drying of the product rich cuts affords the free base as a light brown fluffy solid. The nmr spectrum is consistent with structure. The mass spectrum shows a molecular ion at 718 for the tetrasilylated species.

EXAMPLE 124

N-α-(1-Ethoxycarbonyl-4-methylpentyl)-L-lysyl-L-proline

Dissolve 2-oxo-4-methyl-ethylpentanoate (2.75 g) and N-ε-t-Boc-L-lysyl-L-proline (2.75 g) in 150 ml of ethanol containing 16 g of powdered 4A molecular sieves. Hydrogenate at 40 psi, room temperature, over 1 g of 10% palladium on charcoal. After 1 mole of hydrogen is taken up, filter through filter aid, washing catalyst on the filter cake thoroughly with ethanol. Evaporate solvent to obtain 5.87 g of oil. Suspend oil in water, adjust pH to 8.5 and extract with ethyl acetate (3×60 ml) to remove neutral materials. Adjust pH of aqueous layer to 7, saturate with sodium chloride and extract product with ethyl acetate (3×100 ml). Dry product solution over anhydrous magnesium sulfate. Evaporate ethyl acetate to obtain 4.38 g of crude N-α-(1-ethoxycarbonyl-4-methylpentyl)-N-ε-t-Boc-L-lysyl-L-proline. Remove the t-Boc protecting group in the usual manner with 4 N HCl in ethyl acetate. Convert the resulting hydrochloride salt to the free base with strong acid ion exchange resin (2% pyridine in water elution). Freeze dry product rich cut to obtain 2.1 g of hygroscopic brittle solid. The nmr spectrum is consistent with structure for N-α-(1-carboethoxy-4-methylpentyl)-L-lysyl-L-proline. The mass spectrum gives a peak at 472 for the monosilylated molecular ion plus 1.

EXAMPLE 125

N-α-(1-Carboxy-4-methylpentyl)-L-lysyl-L-proline

N-α-(1-Ethoxycarbonyl-4-methylpentyl)-L-lysyl-L-proline is hydrolyzed to the corresponding carboxylic acid by stirring in an aqueous solution of sodium hydroxide (2.5 equivalents) at room temperature for several days. The reaction mixture is acidified to pH 5, absorbed on strong acid ion exchange resin and eluted with 2% pyridine in water. The product rich-cut is freeze dried to afford N-(1-carboxy-4-methylpentyl)-L-lysyl-L-proline as a white fluffy solid. The nmr spectrum is consistent with structure. The mass spectrum shows a molecular ion at 516 for the disilylated species.

EXAMPLE 126

N-α-(1-Carboxy-3-phenylpropyl)-L-leucyl-L-tryptophan

In the manner described in Example 54, 2-oxo-4-phenylbutyric acid and L-leucyl-L-tryptophan are condensed in the presence of sodium cyanoborohydride. The product is freeze dried from a mixture of dioxane/water since it is only slightly water soluble. The nmr spectrum is consistent with structure. The mass spectrum gives a molecular ion at 695 for the trisilylated species.

EXAMPLE 127

A. Tablet

A typical tablet contains N-(1(S)-ethoxycarbonyl-3-phenylpropyl)-L-alanyl-L-proline (25 mg), pregelatinized starch USP (82 mg), microcrystalline cellulose (82 mg) and magnesium stearate (1 mg). In like manner, for example, N-(1(S)-carboxy-3-phenylpropyl)-L-lysyl-L-proline (20 mg) may be formulated in place of N-(1(S)-ethoxycarbonyl-3-phenylpropyl)-L-alanyl-L-proline with the composition of pregelatinized starch, microcrystalline cellulose and magnesium stearate described above.

B. Combination Tablet

A combination tablet with a diuretic such as hydrochlorothiazide typically contains N-(1(S)-ethoxycarbonyl-3-phenylpropyl)-L-alanyl-L-proline (7.5 mg), hydrochlorothiazide (50 mg), pregelatinized starch USP (82 mg), microcrystalline cellulose (82 mg) and magnesium stearate (1 mg). Tablets with, for example, N-(1(S)-carboxy-3-phenylpropyl)-L-lysyl-L-proline (5 mg) and hydrochlorothiazide (50 mg) are made by substituting the former in place of N-(1(S)-ethoxycarbonyl-3-phenylpropyl in the composition described above.

C. Injection

A typical injectible formulation contains N-(1(S)-carboxyl-3-phenylpropyl)-L-alanine-L-proline (5.42 mg), sodium phosphate diabasic anhydrous (11.4 mg), benzyl alcohol (0.01 ml), and water for injection (1.0 ml). Similarly, this formulation can be prepared employing, for example, N-(1(S)-carboxy-3-phenylpropyl)-L-lysyl-L-proline in place of N-(1(S)-ethoxycarbonyl-3-phenylpropyl)-L-alanyl-L-proline. In addition, such an injectible formulation can also include a pharmaceutically effective amount of another antihypertensive and/or diuretic such as, for example, hydrochlorathiazide as described in B of this Example.

D. Suppository

Typical suppository formulations for rectal administration can contain N-(1(S)-ethoxycarbonyl-3-phenylpropyl)-L-alanyl-L-proline (1–25 mg), butylated hydroxyanisol (0.08–1.0 mg), disodium calcium edetate (0.25–0.5 mg), and polyethylene glycol (775–1600 mg). Other suppository formulations can be made by substituting, for example, N-(1(S)-carboxy-3-phenylpropyl)-L-lysyl-L-proline for N-(1(S)-ethoxycarbonyl-3-phenylpropyl)-L-alanyl-L-proline and by substituting, for example, butylated hydroxytoluene (0.04–0.08 mg) for the disodium calcium edetate and a hydrogenated vegetable oil (675–1400 mg) such as Suppocire L, Wecobee FS, Wecobee M, Witepsols, and the like, for the polyethylene glycol. Further, these suppository formulations can also include another antihypertensive and/or diuretic in pharmaceutically effective amounts as described, for example, in B and C of this Example.

EXAMPLE 128

N-[1-Ethoxycarbonyl-3-(3-indolylpropyl]-L-alanyl-L-proline

A solution of L-alanyl-L-proline (0.35 g) and ethyl 4-(3-indolyl)-2-oxobutyrate (1.0 g) in 30 ml of ethanol was hydrogenated with 10% Pd on carbon in the presence of 3.2 g of powdered molecular sieves (4A) under 40 lbs of hydrogen pressure. After the reaction was complete the slurry was filtered and the filtrate concentrated to dryness. The residual oil was dissolved in 5 ml of methanol and chromatographed on a Sephadex LH-20 column to yield 0.67 g of crude product as an orange oil. A portion of the crude (0.3 g) was purified by solution in water and extraction with ether. Product was recovered by dilution of the aqueous phase with an equal volume of saturated NaCl solution and extraction with ethyl acetate to yield 80 mg of (N-[1-ethoxycarbonyl-3-(3-indolyl)propyl]-L-alanyl-L-proline as a yellow oil. Mass spectral analysis showed peaks at 559 for the di-silylated product and at 631 for the tri-silylated product.

EXAMPLE 129

Benzyl N-(1(S)-carboxy-3-phenylpropyl)-L-alanyl-L-prolinate

Thionyl chloride (13.1 ml) was added to 150 ml of benzyl alcohol keeping the temperature below 0° (exothermic reaction). N-(1(S)-Carboxy-3-phenylpropyl)-L-alanyl-L-proline (15 g) was added portionwise to the cold solution. The cooling bath was removed and the mixture was stirred at room temperature overnight. After heating to 45° under vacuum to remove dissolved gases the reaction was diluted with 500 ml ether and washed with 10×100 ml of water. A solid appeared in the organic layer which was filtered and dried to yield 4.9 g of crude monobenzyl ester.

The combined aqueous extracts neutralized with NaHCO3 gave a second crop weighing 1.4 g. The two crops were combined and a portion (1.0 g) was recrystallized from ethanol-water to yield 0.95 g of pure monobenzyl ester, m.p. 120°–125°. Mass spectral analysis indicated the benzyl ester was attached to the proline ring.

EXAMPLE 130

Ethyl N-(1(S)-ethoxycarbonyl-3-phenylpropyl)-L-alanyl-L-prolinate hydrochloride

A solution of 3.0 g of N-[1-(S)-ethoxycarbonyl-3-phenylpropyl]-L-alanyl-L-proline in 50 ml of absolute ethanol is saturated with HCl gas at 0°. After standing at 0° overnight, the HCl and ethanol was removed under vacuum to afford 3.1 g of an oil which upon freeze-drying gives a white solid. Thin layer chromatography and HPLC indicate only one component. The nmr spectrum indicates two ethyl groups per aromatic ring. The mass spectrum shows a molecular ion at 404 m/e.

EXAMPLE 131

N-[1-Ethoxycarbonyl-3-(2-chlorophenyl)propyl]-L-alanyl-L-proline

In the manner described in Example 26, ethyl-2-oxo-4-(2-chlorophenyl)butyrate and L-alanyl-L-proline are condensed in the presence of sodium cyanoborohydride to yield N-[1-ethoxycarbonyl-3-(2-chlorophenyl)propyl]-L-alanyl-L-proline. The mass spectrum shows a peak at 411, (M+1), and a strong peak at 392, (M-18).

EXAMPLE 132

N-[1-Ethoxycarbonyl-3-(4-fluorophenyl)propyl]-L-alanyl-L-proline

In the manner described in Example 26, ethyl-2-oxo-4-(4-fluoro-phenyl)butyrate and L-alanyl-L-proline are condensed in the presence of sodium cyanoborohydride to yield N-[1-ethoxycarbonyl-3-(4-fluorophenyl)propyl]-L-alanyl-L-proline. The mass spectrum shows a molecular ion at 394, and strong peaks at 376 (M-18, H2O) and 375 (M-19, F). The nmr spectrum is consistent with the proposed structure. Elemental analysis indicates a sesquihydrate.

EXAMPLE 133

N-[1-Ethoxycarbonyl-3-(2-naphthyl)propyl]-L-alanyl-L-proline

In the manner described in Example 26, ethyl-2-oxo-4-(2-naphthyl)-butyrate and L-alanyl-L-proline are condensed in the presence of sodium cyanoborohydride to yield N-[1-ethoxycarbonyl-3-(2-naphthyl)propyl]-L-alanyl-L-proline. The mass spectrum shows a molecular ion at 426 and a peak at 408 (M-18, H2O). The nmr spectrum is consistent with the proposed structure. The elemental analysis indicates a hemihydrate.

EXAMPLE 134

N-α-[1-Carboxy-3-(2-chlorophenyl)propyl]-L-lysyl-L-proline

In the manner described in Example 26, ethyl-2-oxo-4-(2-chloro-phenyl)butyrate and N--t-Boc-L-lysyl-L-proline are condensed in the presence of sodium cyanoborohydride to yield N-α-[1-ethoxycarbonyl-3-(2-chlorophenyl)propyl]-N-ε-t-Boc-L-lysyl-L-proline. The t-Boc protecting group is removed by treatment with 4 N HCl in ethyl acetate, and the ethyl ester group is then saponified with dilute sodium hydroxide to furnish N-α-[1-carboxy-3-(2-chlorophenyl)propyl]-L-lysyl-L-proline after absorption on, and elution from strong acid ion exchange resin. Elemental analysis indicates solvation with 1.5 moles of water. The nmr spectrum is consistent with the proposed structure. The mass spectrum of a silylated sample shows a peak at 568, which corresponds to a loss of mass 15 (methyl) from the disilylated species.

EXAMPLE 135

N-α-[1-Carboxy-3-(4-fluorophenyl)propyl]L-lysyl-L-proline

In the manner described in Example 134, ethyl-2-oxo-4-(4-fluorophenyl)butyrate and N-ε-t-Boc-L-lysyl-L-proline are condensed in the presence of sodium cyanoborohydride. The resulting product is deblocked as in Example 4 to yield N-α-[1-carboxy-3-(4-fluorophenyl)-propyl]-L-lysyl-L-proline. Elemental analysis indicates the sesquihydrate. The nmr spectrum is consistent with the proposed structure. The mass spectrum of a silylated sample shows a molecular ion at 711 for the tetrasilylated species.

EXAMPLE 136

N-α-[1-Carboxy-3-(2-naphthyl)propyl]L-lysyl-L-proline

In the manner described in Example 134, substituting ethyl-2-oxo-4-(2-naphthyl)butyrate for ethyl-2-oxo-4-(2-chlorophenyl)butyrate there is obtained ultimately N-α-[1-carboxy-3-(2-naphthyl)propyl]-L-lysyl-L-proline. The nmr spectrum is consistent with the proposed structure. The mass spectrum shows a molecular ion at 599 for the disilylated species.

EXAMPLE 137

Ethyl 2-oxo-4-(2-thienyl)-butyrate

A mixture of phosphorous tribromide (18.95 g) and pyridine (3.76 cc) in 10 ml of benzene is chilled to $-5°$ C. and treated with a solution of 2-(2-thienyl)-ethanol (25 g) in 10 ml of benzene containing 1.25 cc of pyridine at such a rate that the reaction temperature never exceeds 0° C. The mixture is then allowed to come to room temperature while stirring overnight. The reaction mixture is then concentrated on a water pump at 30°–40° C. to remove solvent and other volatiles, and the residue Claisen-distilled under water pump vacuum to yield 21 g of crude bromide (b.p. 115°–119° C.). This material is then fractionally distilled at 0.3 mm to provide 19 g of pure 2-(2-thienyl)-ethyl bromide (b.p. 50°–51° C.; 99.9% by gc). This bromide is dissolved in 40 ml of dry tetrahydrofuran and added, dropwise, to a stirred mixture of magnesium turnings (2.4 g) and 15 ml of dry tetrahydrofuran under nitrogen atmosphere. The mixture is then stirred and refluxed for 1 hour, cooled to room temperature, and added, dropwise under nitrogen, to a stirred mixture of diethyl oxalate (17.5 g) in 25 ml of dry tetrahydrofuran in a $-15°$ C. bath. After completion the reaction mixture is stirred at $-10°$ C. for 15 minutes, then allowed to warm to 10° C. and treated with 60 ml of saturated ammonium chloride solution. The aqueous layer is extracted twice with toluene; the combined organic layers dried over magnesium sulfate and concentrated in vacuo to provide 16.7 g of a mixture containing by gc analysis: solvent (26%); diethyl oxalate (10.5%); and ethyl 2-oxo-(2-thienyl)-butyrate (63.4%). The nmr spectrum (CDCl$_3$) is consistent for this mixture, showing the presence of two specific types of ethyl esters, and the mass spectrum exhibits a peak at m/e=212 for the molecular ion of one keto-ester along with a fragmentation pattern consistent with structure.

EXAMPLE 138

N-[1-Ethoxycarbonyl-3-(2-thienyl)-propyl]L-alanyl-L-proline 4 g of type 4 A molecular sieves (powdered) are added to a mixture of L-alanyl-L-proline (0.93 g) and ethyl 2-oxo-4-(2-thienyl)-butyrate (3.18 g) in 25 ml of anhydrous ethyl alcohol. The mixture is stirred for 45 minutes at room temperature, followed by slow addition (3.5 hours) of a solution of sodium cyanoborohydride (0.785 g) in 15 ml of anhydrous ethyl alcohol and stirring overnight at room temperature. The reaction mixture is made just slightly acidic with glacial acetic acid, filtered and the filtrate conc. in vacuo to an orange oil. Extraction of a chloroform solution of this oil with 10% potassium bicarbonate, followed by re-extraction of the acidified (pH 3) bicarbonate extracts with chloroform provide, after drying and evaporation of solvent, 400 mg of the desired substituted dipeptide. The nmr spectrum (CDCl$_3$) shows the thienyl proton as multiplet at 7.0 ppm, two active protons in broad singlet at 6.2 ppm, six methyl protons as broad multiplet 1.22–1.43 ppm range, and a series of ill-defined multiplets ranging 1.8–4.4 ppm.

EXAMPLE 139

N[1-Carboxy-3-(2-thienyl)-propyl]-L-lysyl-L-proline 6.95 g of type 4 A molecular sieves (powdered) are added to a mixture of L-N-ε-Boc-lysyl-L-proline (2.98 g) and ethyl 2-oxo-4-(2-thienyl)-butyrate (6.4 g) in 40 ml of anhydrous ethyl alcohol. The mixture is stirred at room temperature for 45 minutes, followed by slow addition (4.5 hours) of a solution of sodium cyanoborohydride (1.36 g) in 25 ml of anhydrous ethyl alcohol and stirring overnight at room temperature. The reaction mixture is then made just slightly acidic with glacial acetic acid, filtered and concentrated in vacuo to an orange foam (16.4 g). Trituration of this crude foam with 3 portions of ether, decanting off the ethereal solution, removed a significant amount of the excess keto-ester present. The ether-insoluble oil is now stirred in 150 ml of 4 N HCl/ethyl acetate at 0° C. for 1 hour and poured into 1.1 of cold ether, filtered, and concentrated in vacuo to an orange oil. A solution of this deblocked material in 250 ml of ethyl alcohol is treated with 5 g sodium hydroxide in 35 ml of water and stirred at room temperature overnight. Careful acidification with 0.5 N HCl, concentration in vacuo and subsequent purification by elution from a column of 150 ml of Dowex 50W-X2 (H+) with water containing 2% pyridine provides the substituted dipeptide as the dicarboxylic acid. The nmr spectrum (D$_2$O/DCl) is consistent with structure.

EXAMPLE 140

N-(1-Carboxy-3-phenylpropyl)-L-alanyl-α-aminoisobutyric acid

Prepare a mixture of 8.9 g methyl α-aminoisobutyrate hydrochloride, 8.7 ml triethylamine and 11.9 g BOC-L-alanine in 135 ml CH$_2$Cl$_2$. Add a solution of 14.2 g dicyclohexylcarbodiimide in 20 ml CH$_2$Cl$_2$ and stir the mixture at room temperature for 48 hours. Filter and concentrate the filtrate, then partition the residue between H$_2$O and ethyl acetate. Wash the organic phase with 10% citric acid, H₂O, 5% sodium bicarbonate and H₂O. Dry over MgSO₄ and concentrate to obtain the crude dipeptide. Purify the crude product on silica gel eluting with hexane-ethyl acetate (7:3).

Dissolve 1.2 g of this dipeptide in 30 ml 4 N HCl/ethyl acetate and store for 1 hour at room temperature. Concentrate the mixture and freeze dry the residue from H₂O to obtain L-alanyl-α-aminoisobutyric acid methyl ester hydrochloride.

Prepare a solution of 688 mg of this amino ester, 949 mg ethyl 2-oxo-4-phenylbutyrate and 328 mg sodium acetate in 10 ml ethanol. Hydrogenate this mixture over 0.5 g 10% palladium on charcoal catalyst at 40 psig. Filter and concentrate the filtrate. Add 4 ml 7:3 hexane:ethyl acetate, filter and chromatograph the filtrate on silica gel to obtain methyl N-(1-ethoxycarbonyl-3-phenylpropyl)-(L)-alanyl-α-amino-isobutyrate.

Analysis Calc. (C₂₀H₃₀N₂O₅): C, 63.30; H, 8.24; N, 7.38. Found: C, 63.58; H, 8.13; N, 7.27. The nmr spectrum is consistent with structure.

Stir 460 mg of this diester with 3 ml 2 N NaOH overnight at room temperature. Apply the resulting solution to a Dowex 50 (H⁺) column and elute the 5% pyridine in H₂O. Concentrate the appropriate fractions to obtain N-(-1-carboxy-3-phenylpropyl)-L-alanyl-α-aminoisobutyric acid.

Analysis Cal. (C₁₇H₂₇N₂O₅.2H₂O): C, 54.82; H, 7.58; N, 7.52. Found: C, 54.94; H, 7.50; N, 7.48. Nmr is consistent with structure.

EXAMPLE 141

N-(1-Carboxy-3-phenylpropyl)-L-alanyl-L-α-methyl-phenylalanine

Prepare this compound as described in Example 140 starting with L-α-methylphenylalanine methyl ester hydrochloride in place of α-aminoisobutyric acid methyl ester hydrochloride.

EXAMPLE 142

N-{1-Carboxy-3-[4-(1-benzylimidazolyl)]propyl}-L-alanyl-L-proline

An excess of 4-[4-(1-benzylimidazolyl)]-2-ketobutyric acid (prepared by dibenzylation of 3-(4-imidazolyl)propionic acid and subsequent condensation with diethyl oxalate, followed by acid catalyzed hydrolysis and decarboxylation) is condensed with L-alanyl-L-proline in water (pH 6.7) in the presence of excess NaBH₃CN. After 3 days at room temperature, the product is absorbed on a strong acid ion-exchange resin. Elution with 2% aqueous pyridine and freeze-drying gives the crude product which is further purified on a Sephadex LH-20 column using MeOH. The C¹³ and H¹ NMR and IR spectral data are consistent with the structure. A satisfactory combustion analysis is obtained for the mono-hydrate. The mass spectrum (after silylation) shows peaks at 572 (M+), 557 (M+−15) and 455 (M±Co₂SiMe₃) m/e.

EXAMPLE 143

N-[1-Carboxy-3-(4-imidazolyl)propyl]-L-alanyl-L-proline

The N-[1-carboxy-3-[4-(1-benzylimidazolyl)propyl]-L-alanyl-L-proline (prepared as described in Example 142 above) was subjected to hydrogenolysis at 40 psig. over an equal weight of 5% Pd/C in a 3:1 HOAc/H₂O mixture at 60° for 3 days. After removal of the catalyst by filtration and concentration of the filtrate, the crude product was purified by absorption on a strong acid ion-exchange resin followed by elution with 2% aqueous pyridine and freeze-drying. Further purification was obtained on a Sephadex LH-20 column using MeOH. A H¹NMR and TLC (silica gel) analysis indicated that the benzyl group had been removed to yield the titled product. The mass spectrum showed a peak for (M+−18) at m/e 320.

EXAMPLE 144

N-{1-Carboxy-3-[4-(1-benzylimidazolyl)]propyl}-L-lysyl-L-proline and
N-[1-carboxy-3-(4-imidazolyl)propyl]-L-lysyl-L-proline Both of the titled compounds are prepared in the same manner as N-{1-carboxy-3-[4-(1-benzylimidazolyl)]propyl}-L-alanyl-L-proline (Example 142) and N-[1-carboxy-3-(4-imidazolyl)propyl]-L-alanyl-L-proline substituting Et-BOC-L-lysyl-L-proline for L-alanyl-L-proline and removing the t-BOC group with trifluoroacetic acid at 0° for 3 hrs. after the condensation step.

EXAMPLE 145

N-{1-Ethoxycarbonyl-3-[4-(1-benzylimidazolyl)-propyl}-L-alanyl-L-proline and
N-[1-ethoxycarbonyl-3-(4-imidazolyl)propyl]-L-alanyl-L-proline Both of the titled compounds are prepared in the same manner as N-{1-carboxy-3-[4-(1-benzylimidazolyl)]propyl}-L-alanyl-L-proline (Example 142) and N-[1-carboxy-3-(4-imidazolyl)propyl]-L-alanyl-L-proline (Example 143) using the ethyl ester of 4-[4-(1-benzylimidazolyl)]-2-ketobutyric acid and running the condensation in EtOH (in the presence of 4A sieves) instead of water.

What is claimed is:

1. A compound of the formula:

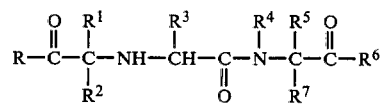

wherein
R and R⁶ are the same or different and are hydroxy,
  lower alkoxy,
  lower alkenoxy,
  diloweralkylamino lower alkoxy,
  acylamino lower alkoxy,
  acyloxy lower alkoxy,
  aryloxy,
  arloweralkyloxy
  substituted aryloxy or substituted arloweralkoxy wherein the substituent is methyl, halo, or methoxy,
  amino,
  loweralkylamino
  diloweralkylamino,
  arloweralkylamino or
  hydroxyamino;
R¹ is hydrogen,
  alkyl of from 1 to 20 carbon atoms, including branched, cyclic and unsaturated alkyl groups;
  substituted lower alkyl wherein the substituent is halo hydroxy
lower alkoxy
aryloxy
amino
loweralkylamino
diloweralkylamino
acylamino
arylamino
guanidino
imidazolyl,
indolyl,
mercapto,
loweralkylthio
arylthio
carboxy
carboxamido
carboloweralkoxy
phenyl
substituted phenyl wherein the substituent is
  lower alkyl
  lower alkoxy or
  halo;
arloweralkyl or heteroarloweralkyl,
arloweralkenyl or heteroarloweralkenyl,
substituted arloweralkyl, substituted heteroarloweralkyl, substituted arloweralkenyl or substituted heteroarloweralkenyl, wherein the substituent is
  halo or dihalo
  lower alkyl
  hydroxy
  lower alkoxy
  amino
  aminomethyl
  acylamino
  diloweralkylamino
  loweralkylamino
  carboxyl
  halo loweralkyl
  cyano or
  sulfonamido;
arloweralkyl or heteroarloweralkyl substituted on the alkyl portion by amino or acylamino;
$R^2$ and $R^7$ are hydrogen or lower alkyl;
$R^3$ is hydrogen
  lower alkyl
  phenyl lower alkyl
  aminomethyl phenyl lower alkyl
  hydroxy phenyl lower alkyl
  hydroxy lower alkyl
  acetylamino lower alkyl
  acylamino lower alkyl
  amino lower alkyl
  dimethylamino lower alkyl
  halo lower alkyl
  guanidino lower alkyl
  imidazolyl lower alkyl
  indolyl lower alkyl
  mercapto lower alkyl and
  loweralkylthio lower alkyl;
$R^4$ is hydrogen or
  lower alkyl;
$R^5$ is hydrogen
  lower alkyl
  phenyl
  phenyl lower alkyl
  hydroxy phenyl lower alkyl
  hydroxy lower alkyl
  amino lower alkyl
  guanidino lower alkyl
  imidazolyl lower alkyl
  indolyl lower alkyl
  mercapto lower alkyl or
  loweralkyl thio lower alkyl;
$R^4$ and $R^5$ may be connected together to form an alkylene bridge of from 2 to 4 carbon atoms, an alkylene bridge of from 2 to 3 carbon atoms and one sulphur atom, an alkylene bridge of from 3 to 4 carbon atoms containing a double bond or an alkylene bridge as above, substituted with
  hydroxy
  lower alkoxy
  lower alkyl or
  dilower alkyl
and the pharmaceutically acceptable salts thereof wherein said aryl is a member selected from the group consisting of phenyl or naphthyl and said heteroaryl is a member selected from the group consisting of pyridyl, thienyl, furyl, indolyl, benzthienyl, imidazolyl, or thiazolyl.

2. Compounds of claim 1 in which the carbon bearing $R^1$ is of the S configuration and the other absolute configurations are those of L-amino acids.

3. A compound of the formula:

$$R-\overset{O}{\underset{}{C}}-\overset{R^1}{\underset{R^2}{C}}-NH-CH-\overset{R^3}{\underset{\overset{\|}{O}}{C}}-N-\overset{R^4}{\underset{R^7}{C}}-\overset{R^5}{\underset{}{C}}-\overset{O}{\underset{}{C}}-R^6$$

wherein
R and $R^6$ can each independently be hydroxy, lower alkoxy,
  lower alkenoxy,
  arloweralkyloxy,
  amino,
  diloweralkylamino lower alkoxy,
  acylamino lower alkoxy or
  acyloxy lower alkoxy,
$R^1$ is hydrogen,
  alkyl of from 1 to 20 carbon atoms, including branched, cyclic and unsaturated alkyl groups;
substituted lower alkyl wherein the substituent is
  halo
  hydroxy
  lower alkoxy
  aryloxy
  amino
  loweralkylamino
  diloweralkylamino
  acylamino
  arylamino
  guanidino
  imidazoyl,
  indolyl,
  mercapto,
  loweralkylthio
  arylthio
  carboxy
  carboxamido or
  carbolower alkoxy
  phenyl
  substituted phenyl wherein the substituent is
    lower alkyl
    lower alkoxy or
    halo;

arloweralkyl or heteroaryloweralkyl arloweralkenyl
or heteroarloweralkenyl, substituted arloweralkyl,
substituted heteroarylloweralkyl, substituted arloweralkenyl or substituted heteroarloweralkenyl,
wherein the substituent is halo or dihalo
  lower alkyl
  hydroxy
  lower alkoxy
  amino
  aminomethyl
  acylamino
  diloweralkylamino
  loweralkylamino
  carboxyl
  halo alkyl
  cyano or
  sulfonamido
arloweralkyl or heteroarloweralkyl substituted on the alkyl portion by amino or acylamino;
$R^2$ and $R^7$ are hydrogen;
$R^3$ is lower alkyl, amino lower alkyl, imidazolyl, lower alkyl, halo lower alkyl;
$R^4$ and $R^5$ are joined to form an alkylene bridge of from 2 to 4 carbon atoms or an alkylene bridge of from 2 to 3 carbon atoms and one sulfur atom or an alkylene bridge of from 2 to 3 carbon atoms and one sulfur atom or an alkylene bridge of from 3 to 4 carbon atoms containing a double bond or an alkylene bridge of from 3 to 4 carbon atoms containing a double bond or an alkylene bridge as above substituted with hydroxy, lower alkoxy or lower alkyl,
or the pharmaceutically acceptable salts thereof wherein said aryl is a member selected from the group consisting of phenyl or naphthyl and said heteroaryl is a member selected from the group consisting of pyridyl, thienyl, furyl, indolyl, benzthienyl, imidazoyl, or thiazolyl.

4. Compounds of claim 3 in which the carbon bearing $R^1$ is of the S configuration and the other absolute configurations are those of L-amino acids.

5. A compound of claim 3 wherein $R^4$ and $R^5$ are joined through the carbon and nitrogen atoms to which they are attached to form a ring of the formulae:

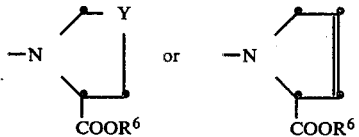

wherein Y is $CH_2$, S, or $CH—OCH_3$ and R, $R^1$, $R^2$, $R^3$, $R^6$ and $R^7$ are as defined in claim 3.

6. Compounds of claim 5 in which the carbon bearing $R^1$ is of the S configuration and the other absolute configurations are those of L-amino acids.

7. A compound of the formula:

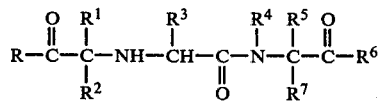

wherein
R and $R^6$ can each independently be hydroxy, lower alkoxy,
  lower alkenoxy,
  arloweralkyloxy,
  amino,
  diloweralkylamino lower alkoxy,
  acylamino lower alkoxy or
  acyloxy lower alkoxy,
$R^1$ is alkyl having from 1-8 carbon atoms, substituted lower alkyl wherein the alkyl group has 1-5 carbon atoms and the substituent is amino, arylthio, aryloxy or arylamino, aralkyl or heteroaralkyl wherein the alkyl portion has 1-3 carbon atoms, substituted aralkyl or heteroaralkyl wherein the alkyl groups have 1-3 carbon atoms and the substituent(s) is halo, dihalo, amino, aminoalkyl, hydroxy, lower alkoxy or lower alkyl;
$R^2$ and $R^7$ are hydrogen;
$R^3$ is lower alkyl or amino lower alkyl;
$R^4$ and $R^5$ can be joined together through the carbon and nitrogen atoms to which they are attached to form a ring of the formula:

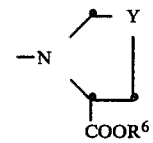

wherein Y is $CH_2$, S, or $CH—OCH_3$ or the pharmaceutically acceptable salts thereof wherein said aryl is a member selected from the group consisting of phenyl or naphthyl and said heteroaryl is a member selected from the group consisting of pyridyl, thienyl, furyl, indolyl, benzthienyl, imidazoyl or thiazolyl.

8. Compounds of claim 7 in which the carbon bearing $R^1$ is of the S configuration and the other absolute configurations are those of L-amino acids.

9. A compound of the formula:

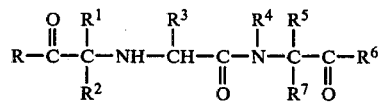

wherein
R and $R^6$ can each independently be hydroxy, lower alkoxy, aralkyloxy,
$R^2$ and $R^7$ are hydrogen,
$R^3$ is methyl, aminoloweralkyl,
$R^4$ and $R^5$ are joined through the carbon and nitrogen atoms to form proline, 4-thiaproline or 4-methoxyproline, and
$R^1$ is alkyl having from 1-8 carbon atoms, substituted lower alkyl wherein the alkyl group has 1-5 carbon atoms and the substituent is amino, arylthio or aryloxy, aralkyl or heteroaralkyl wherein the alkyl portion has 1-3 carbon atoms, substituted aralkyl or heteroaralkyl wherein the alkyl groups have 1-3 carbon atoms and the substituent(s) is halo, dihalo, amino, aminoalkyl, hydroxy, lower alkoxy or lower alkyl;
and the pharmaceutically acceptable salts thereof wherein said aryl is a member selected from the group consisting of phenyl or naphthyl and said heteroaryl is a member selected from the group consisting of pyridyl, thienyl, furyl, indolyl, benzthienyl, imidazoyl or thiazolyl.

10. Compounds of claim 9 in which the carbon bearing $R^1$ is of the S configuration and the other absolute configurations are those of L-amino acids.

11. A compound of claim 9 which is N-(1-carboxy-3-phenylpropyl)-L-alanyl-L-proline.

12. A compound of claim 9 which is N-(1-ethoxycarbonyl-3-phenylpropyl)-L-alanyl-L-proline.

13. A compound of claim 9 which is N-(1-ethoxycarbonyl)-4-methylpentyl-L-alanyl-L-proline.

14. A compound of claim 9 which is N-(1carboxy-5-aminopentyl)-L-alanyl-L-proline.

15. A compound of claim 9 which is N-α-(1-carboxy-3-phenylpropyl)-L-lysyl-L-proline.

16. A compound of claim 9 which is N-α-(1-ethoxycarbonyl-3-phenylpropyl)-L-lysyl-L-proline.

17. A compound of claim 9 which is N-α-[1-carboxy-3-(3-indolyl)-propyl]-L-lysyl-L-proline.

18. A compound of claim 9 which is N-α-[1-carboxy-3-(4-chlorophenyl)-propyl]-L-lysyl-L-proline.

19. A compound of claim 9 which is N-α-[1-carboxy-2-phenylthioethyl]-L-lysyl-L-proline.

20. A compound of claim 9 which is N-α-[1-carboxy-3-(4-chlorophenyl)-propyl]-L-lysyl-trans-4-methoxy-L-proline.

21. A compound of claim 9 which is N-α-[1-carboxy-5-aminopentyl]-L-lysyl-L-proline.

22. A compound of claim 9 which is N-α-(1-carboxy-3-phenylpropyl)-L-ornithyl-L-proline.

23. A compound of claim 9 which is ethyl N-(1-ethoxycarbonyl-3-phenylpropyl)-L-alanyl-L-prolinate hydrochloride.

24. A compound of claim 9 which is N-[1-(ethoxycarbonyl)-3-(4-imidazolyl)propyl]-L-alanyl-L-proline.

25. A compound of claim 9 which is N-[1-(carboxy-3-(4-imidazolyl)propyl]-L-lysyl-L-proline.

26. The compound: N-(1(S)-carboxy-3-phenylpropyl)-L-alanyl-L-proline.

27. The compound: N-(1(S)-ethoxycarbonyl-3-phenylpropyl)-L-alanyl-L-proline.

28. The compound: N-(1(S)-ethoxycarbonyl-3-phenylpropyl)-L-alanyl-L-proline maleate salt.

29. The compound: N-α-(1(S)-carboxy-3-phenylpropyl)-L-lysyl-L-proline.

30. The compound: ethyl-N-(1(S)-ethoxycarbonyl-3-phenylpropyl)-L-alanyl-L-prolinate hydrochloride.

31. The compound: N-α-(1(S)-ethoxycarbonyl-3-phenylpropyl)-L-lysyl-L-proline.

32. A pharmaceutical composition useful in the treatment of hypertension which comprises a pharmaceutically acceptable carrier and a pharmaceutically effective amount of a compound of the formula:

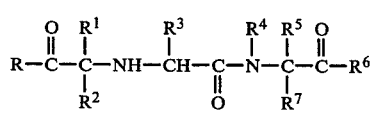

wherein
R and $R^6$ are the same or different and are hydroxy,
 lower alkoxy,
 lower alkenoxy,
 diloweralkylamino lower alkoxy,
 acylamino lower alkoxy,
 acyloxy lower alkoxy,
 aryloxy,
 arloweralkyloxy
 substituted aryloxy or substituted arloweralkoxy wherein the substituent is methyl, halo, or methoxy,
 amino,
 loweralkylamino
 diloweralkylamino,
 arloweralkylamino or
 hydroxyamino;
$R^1$ is hydrogen,
 alkyl of from 1 to 20 carbon atoms, including branched, cyclic and unsaturated alkyl groups;
 substituted lower alkyl wherein the substituent is
  halo
  hydroxy
  lower alkoxy
  aryloxy
  amino
  loweralkylamino
  diloweralkylamino
  acylamino
  arylamino
  guanidino
  imidazolyl,
  indolyl,
  mercapto,
  loweralkylthio
  arylthio
  carboxy
  carboxamido
  carboloweralkoxy
 phenyl
 substituted phenyl wherein the substituent is
  lower alkyl
  lower alkoxy or
  halo;
 arloweralkyl or heteroarloweralkyl,
 arloweralkenyl or heteroarloweralkenyl,
 substituted arloweralkyl, substituted heteroarloweralkyl, substituted arloweralkenyl or substituted heteroarloweralkenyl, wherein the substituent is
  halo or dihalo
  lower alkyl
  hydroxy
  lower alkoxy
  amino
  aminomethyl
  acylamino
  diloweralkylamino
  loweralkylamino
  carboxyl
  halo loweralkyl
  cyano or
  sulfonamido;
 arloweralkyl or heteroarloweralkyl substituted on the alkyl portion by amino or acylamino;
$R^2$ and $R^7$ are hydrogen or lower alkyl;
$R^3$ is hydrogen
 lower alkyl
 phenyl lower alkyl
 aminomethyl pheny lower alkyl
 hydroxy phenyl lower alkyl
 hydroxy lower alkyl
 acetylamino lower alkyl
 acylamino lower alkyl
 amino lower alkyl
 dimethylamino lower alkyl
 guanidino lower alkyl
 halo lower alkyl imidazolyl lower alkyl
indolyl lower alkyl
mercapto lower alkyl and
loweralkylthio lower alkyl;

$R^4$ is hydrogen or
lower alkyl;

$R^5$ is hydrogen
lower alkyl
phenyl
phenyl lower alkyl
hydroxy phenyl lower alkyl
hydroxy lower alkyl
amino lower alkyl
guanidino lower alkyl
imidazolyl lower alkyl
indolyl lower alkyl
mercapto lower alkyl or
loweralkyl thio lower alkyl;

$R^4$ and $R^5$ may be connected together to form an alkylene bridge of from 2 to 4 carbon atoms, an alkylene bridge of from 2 to 3 carbon atoms and one sulphur atom, an alkylene bridge of from 3 to 4 carbon atoms containing a double bond or an alkylene bridge as above, substituted with
hydroxy
lower alkoxy or
lower alkyl
and the pharmaceutically acceptable salts thereof wherein said aryl is a member selected from the group consisting of phenyl or naphthyl and said heteroaryl is a member selected from the group consisting of pyridyl, thienyl, furyl, indolyl, benzthienyl, imidazoyl, or thiazolyl.

33. A pharmaceutical composition useful in the treatment of hypertension which comprises a pharmaceutically acceptable carrier and a pharmaceutically effective amount of a compound of the formula:

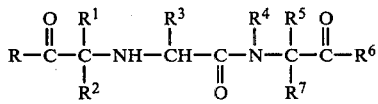

wherein
R and $R^6$ can each independently be hydroxy, lower alkoxy,
lower alkenoxy,
arloweralkyloxy,
amino,
diloweralkylamino lower alkoxy,
acylamino lower alkoxy or
acyloxy lower alkoxy, $R^1$ is alkyl having from 1-8 carbon atoms, substituted lower alkyl wherein the alkyl group has 1-5 carbon atoms and the substituent is amino, arylthio, aryloxy or arylamino, aralkyl or heteroaralkyl wherein the alkyl portion has 1-3 carbon atoms, substituted aralkyl or heteroaralkyl wherein the alkyl groups have 1-3 carbon atoms and the substituent(s) is halo, dihalo, amino, aminoalkyl, hydroxy, lower alkoxy or lower alkyl;

$R^2$ and $R^7$ are hydrogen;

$R^3$ is lower alkyl or amino lower alkyl;

$R^4$ and $R^5$ can be joined together through the carbon and nitrogen atoms to which they are attached to form a ring of the formula:

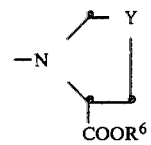

wherein Y is $CH_2$, S, or $CH-OCH_3$ or the pharmaceutically acceptable salts thereof wherein said aryl is a member selected from the group consisting of phenyl or naphthyl and said heteroaryl is a member selected from the group consisting of pyridyl, thienyl, furyl, indolyl, benzthienyl, imidazoyl or thiazolyl.

34. A pharmaceutical composition useful in the treatment of hypertension which comprises a pharmaceutically acceptable carrier and a pharmaceutically effective amount of a compound of the formula:

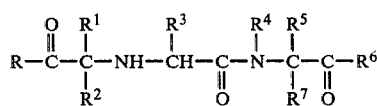

wherein
R and $R^6$ can each independently be hydroxy, lower alkoxy, aralkyloxy, $R^2$ and $R^7$ are hydrogen, $R^3$ is methyl, aminoloweralkyl, $R^4$ and $R^5$ are joined through the carbon and nitrogen atoms to form proline, 4-thiaproline or 4-methoxyproline, and $R^1$ is alkyl having from 1-8 carbon atoms, substituted lower alkyl wherein the alkyl group has 1-5 carbon atoms and the substituent is amino, arylthio or aryloxy, aralkyl or heteroaralkyl wherein the alkyl portion has 1-3 carbon atoms, substituted aralkyl or heteroaralkyl wherein the alkyl groups have 1-3 carbon atoms and the substituent(s) is halo, dihalo, amino, aminoalkyl, hydroxy, lower alkoxy or lower alkyl;

and the pharmaceutically acceptable salts thereof wherein said aryl is a member selected from the group consisting of phenyl or naphthyl and said heteroaryl is a member selected from the group consisting of pyridyl, thienyl, furyl, indolyl, benzthienyl, imidazoyl or thiazolyl.

35. The composition of claim 34 wherein said compound is N-(1-carboxy-3-phenylpropyl)-L-alanyl-L-proline.

36. The composition of claim 34 wherein said compound is N-(1-ethoxycarbonyl-3-phenylpropyl)-L-alanyl-L-proline.

37. The composition of claim 34 wherein said compound is N-(1-ethoxycarbonyl)-4-methylpentyl-L-alanyl-L-proline.

38. The composition of claim 34 wherein said compound is N-(1-carboxy-5-aminopentyl)-L-alanyl-L-proline.

39. The composition of claim 34 wherein said compound is N-α-(1-carboxy-3-phenylpropyl)-L-lysyl-L-proline.

40. The composition of claim 34 wherein said compound is N-α-(1-ethoxycarbonyl-3-phenylpropyl)-L-lysyl-L-proline.

41. The composition of claim 34 wherein said compound is N-α-[1-carboxy-3-(3-indolyl)-propyl]-L-lysyl-L-proline.

42. The composition of claim 34 wherein said compound is N-α-[1-carboxy-3-(4-chlorophenyl)-propyl]-L-lysyl-L-proline.

43. The composition of claim 34 wherein said compound is N-α-[1-carboxy-2-phenylthioethyl]-L-lysyl-L-proline.

44. The composition of claim 34 wherein said compound is N-α-[1-carboxy-3-(4-chlorophenyl)-propyl]-L-lysyl-trans-4-methoxy-L-proline.

45. The composition of claim 34 wherein said compound is N-α-[1-carboxy-5-aminopentyl]-L-lysyl-L-proline.

46. The composition of claim 34 wherein said compound is N-α-(1-carboxy-3-phenylpropyl)-L-ornithyl-L-proline.

47. The composition of claim 34 wherein said compound is ethyl N-(1-ethoxycarbonyl-3-phenylpropyl)-L-alanyl-L-prolinate hydrochloride.

48. The composition of claim 34 wherein said compound is N-α-(1-carboxy-3-phenylpropyl)-L-ornithyl-L-proline.

49. The composition of claim 34 wherein said compound is ethyl N-(1-ethoxycarbonyl-3-phenylpropyl)-L-alanyl-L-prolinate hydrochloride.

50. The composition of claim 34 wherein said compound is N-[1-ethoxycarbonyl)-3-(4-imidazolyl)propyl]-L-alanyl-L-proline.

51. The composition of claim 34 wherein said compound is N-[1-carboxy-3-4-imidazolyl)propyl]-L-lysyl-L-proline.

52. The composition of claim 34 wherein said compound is N-(1(S)-carboxy-3-phenylpropyl)-L-alanyl-L-proline.

53. The composition of claim 34 wherein said compound is N-(1(S)-ethoxycarbonyl-3-phenyl-propyl)-L-alanyl-L-proline.

54. The composition of claim 34 wherein said compound is N-(1(S)-ethoxycarbonyl-3-phenylpropyl)-L-alanyl-L-proline maleate salt.

55. The composition of claim 34 wherein said compound is N-α-(1(S)-carboxy-3-phenylpropyl)-L-lysyl-L-proline.

56. The composition of claim 34 wherein said compound is ethyl N-(1(S)-ethoxycarbonyl-3-phenyl-propyl)-L-alanyl-L-prolinate hydrochloride.

57. The composition of claim 34 wherein said compound is N-α-(1(S)-ethoxycarbonyl-3-phenylpropyl)-L-lysyl-L-proline.

58. A method for treating hypertension which comprises administering to a patient in need of such treatment a pharmaceutically effective amount of a compound of the formula:

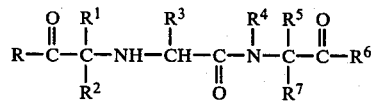

wherein
R and $R^6$ are the same or different and are hydroxy,
lower alkoxy,
lower alkenoxy,
diloweralkylamino lower alkoxy,
acylamino lower alkoxy,
acyloxy lower alkoxy,
aryloxy,
arloweralkyloxy
substituted aryloxy or substituted arloweralkoxy wherein the substituent is methyl, halo, or methoxy,
amino,
loweralkylamino
diloweralkylamino,
arloweralkylamino or
hydroxyamino;
$R^1$ is hydrogen,
alkyl of from 1 to 20 carbon atoms, including branched, cyclic and unsaturated alkyl groups;
substituted lower alkyl wherein the substituent is
halo
hydroxy
lower alkoxy
aryloxy
amino
loweralkylamino
diloweralkylamino
acylamino
arylamino
guanidino
imidazolyl,
indolyl,
mercapto,
loweralkylthio
arylthio
carboxy
carboxamido
carboloweralkoxy
phenyl
substituted phenyl wherein the substituent is
lower alkyl
lower alkoxy or
halo;
arloweralkyl or heteroarloweralkyl,
arloweralkenyl or heteroarloweralkenyl,
substituted arloweralkyl, substituted heteroarloweralkyl, substituted arloweralkenyl or substituted heteroarloweralkenyl, wherein the substituent is
halo or dihalo
lower alkyl
hydroxy
lower alkoxy
amino
aminomethyl
acylamino
diloweralkylamino
loweralkylamino
carboxyl
halo loweralkyl
cyano or
sulfonamido;
arloweralkyl or heteroarloweralkyl substituted on the alkyl portion by amino or acylamino;
$R^2$ and $R^7$ are hydrogen or lower alkyl;
$R^3$ is hydrogen
lower alkyl
phenyl lower alkyl
aminomethyl pheny lower alkyl
hydroxy phenyl lower alkyl
hydroxy lower alkyl
acetylamino lower alkyl
acylamino lower alkyl
amino lower alkyl dimethylamino lower alkyl
guanidino lower alkyl
halo lower alkyl
imidazolyl lower alkyl
indolyl lower alkyl
mercapto lower alkyl and
loweralkylthio lower alkyl;
R⁴ is hydrogen or
lower alkyl;
R⁵ is hydrogen
lower alkyl
phenyl
phenyl lower alkyl
hydroxy phenyl lower alkyl
hydroxy lower alkyl
amino lower alkyl
guanidino lower alkyl
imidazolyl lower alkyl
indolyl lower alkyl
mercapto lower alkyl or
loweralkyl thio lower alkyl;
R⁴ and R⁵ may be connected together to form an alkylene bridge of from 2 to 4 carbon atoms, an alkylene bridge of from 2 to 3 carbon atoms and one sulphur atom, an alkylene bridge of from 3 to 4 carbon atoms containing a double bond or an alkylene bridge as above, substituted with
hydroxy
lower alkoxy or
lower alkyl
and the pharmaceutically acceptable salts thereof wherein said aryl is a member selected from the group consisting of phenyl or naphthyl and said heteroaryl is a member selected from the group consisting of pyridyl, thienyl, furyl, indolyl, benzthienyl, imidazolyl, or thiazolyl.

59. A method of treating hypertension which comprises administering to a patient in need of such treatment a pharmaceutically effective amount of a compound of the formula:

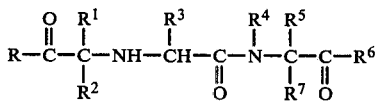

wherein
R and R⁶ can each independently be hydroxy, lower alkoxy, aralkyloxy,
R¹ is alkyl having from 1–8 carbon atoms, substituted lower alkyl wherein the alkyl group has 1–5 carbon atoms and the substituent is amino, arylthio or aryloxy, aralkyl or heteroaralkyl wherein the alkyl portion has 1–3 carbon atoms, substituted aralkyl or heteroaralkyl wherein the alkyl groups have 1–3 carbon atoms and the substituent(s) is halo, dihalo, amino, aminoalkyl, hydroxy, lower alkoxy or lower alkyl;
R² and R⁷ are hydrogen,
R³ is methyl, aminoloweralkyl,
R⁴ and R⁵ can be joined together through the carbon and nitrogen atoms to which they are attached to form proline, 4-thiaproline or 4-methoxyproline or the pharmaceutically acceptable salts thereof wherein said aryl is a member selected from the group consisting of phenyl or naphthyl and said heteroaryl is a member selected from the group consisting of pyridyl, thienyl, furyl, indolyl, benzthienyl, imidazoyl or thiazolyl.

60. The method of claim 59 wherein said compound is N-(1-carboxy-3-phenylpropyl)-L-alanyl-L-proline.

61. The method of claim 59 wherein said compound is N-(1-ethoxycarbonyl-3-phenylpropyl)-L-alanyl-L-proline.

62. The method of claim 59 wherein said compound is N-(1-ethoxycarbonyl)-4-methylpentyl-L-alanyl-L-proline.

63. The method of claim 59 wherein said compound is N-(1-carboxy-5-aminopentyl)-L-alanyl-L-proline.

64. The method of claim 59 wherein said compound is N-α-(1-carboxy-3-phenylpropyl)-L-lysyl-L-proline.

65. The method of claim 59 wherein said compound is N-α-(1-ethoxycarbonyl-3-phenylpropyl)-L-lysyl-L-proline.

66. The method of claim 59 wherein said compound is N-α-[1-carboxy-3-(3-indolyl)-propyl]-L-lysyl-L-proline.

67. The method of claim 59 wherein said compound is N-α-[1-carboxy-3-(4-chlorophenyl)-propyl]-L-lysyl-L-proline.

68. The method of claim 59 wherein said compound is N-α-[1-carboxy-2-phenylthioethyl]-L-lysyl-L-proline.

69. The method of claim 59 wherein said compound is N-α-[1-carboxy-3-(4-chlorophenyl)-propyl]-L-lysyl-trans-4-methoxy-L-proline.

70. The method of claim 59 wherein said compound is N-α-[1-carboxy-5-aminopentyl]-L-lysyl-L-proline.

71. The method of claim 59 wherein said compound is N-α-(1-carboxy-3-phenylpropyl)-L-ornithyl-L-proline.

72. The method of claim 59 wherein said compound is ethyl N-(1-ethoxy carbonyl-3-phenylpropyl)-L-alanyl-L-prolinate hydrochloride.

73. The method of claim 59 wherein said compound is N-α-(1-carboxy-3-phenylpropyl)-L-ornithyl-L-proline.

74. The method of claim 59 wherein said compound is ethyl N-(1-ethoxycarbonyl-3-phenylpropyl)-1-alanyl-L-prolinate hydrochloride.

75. The method of claim 59 wherein said compound is N-[1-(ethoxycarbonyl)-3-(4-imidazolyl)propyl]-L-alanyl-L-proline.

76. The method of claim 59 wherein said compound is N-[1-carboxy-3-(4-imidazolyl)propyl]-L-lysyl-L-proline.

77. The method of claim 59 wherein said compound is N-(1(S)-carboxy-3-phenylpropyl)-L-alanyl-L-proline.

78. The method of claim 59 wherein said compound is N-(1(S)-ethoxycarbonyl-3-phenylpropyl)-L-alanyl-L-proline.

79. The method of claim 59 wherein said compound is N-(1(S)-ethoxycarbonyl-3-phenylpropyl)-L-alanyl-L-proline maleate salt.

80. The method of claim 59 wherein said compound is N-(1(S)-carboxy-3-phenylpropyl)-L-lysyl-L-proline.

81. The method of claim 59 wherein said compound is ethyl N-(1(S)-ethoxycarbonyl-3-phenylpropyl)-L-alanyl-L-prolinate hydrochloride.

82. The method of claim 59 wherein said compound is N-α-(1(S)-ethoxycarbonyl-3-phenylpropyl)-L-lysyl-L-proline.

* * * * *

UNITED STATES PATENT AND TRADEMARK OFFICE
CERTIFICATE OF CORRECTION

PATENT NO. : 4,374,829                  Page 1 of 2
DATED : February 22, 1983
INVENTOR(S) : Elbert E. Harris, Arthur A. Patchett, Edward W. Tristram and Matthew J. Wyvratt It is certified that error appears in the above-identified patent and that said Letters Patent is hereby corrected as shown below:

At Column 3, lines 36-44

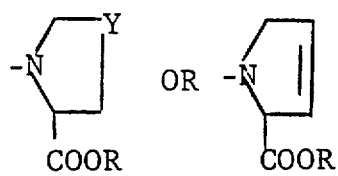  should read  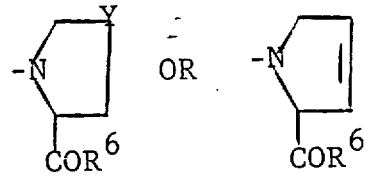

At Claim 3, Column 55, lines 25-27, after "sulfur atom" delete "or ... sulfur atom".

At Claim 5, Column 55, lines 45-52

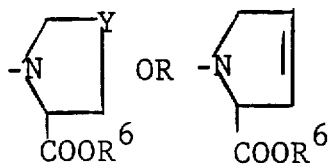  should read  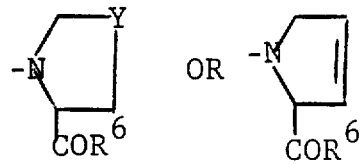

UNITED STATES PATENT AND TRADEMARK OFFICE
CERTIFICATE OF CORRECTION

PATENT NO. : 4,374,829

DATED : February 22, 1983

INVENTOR(S) : Elbert E. Harris, Arthur A. Patchett, Edward W. Tristram and Matthew J. Wyvratt It is certified that error appears in the above-identified patent and that said Letters Patent is hereby corrected as shown below:

At Claim 7, Column 56, lines 20-28 and at Claim 33, Column 60, lines 1-8

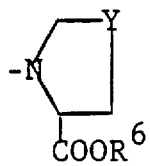     should read     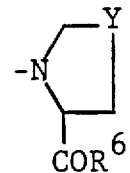

Signed and Sealed this

Seventh Day of June, 1988

Attest:

DONALD J. QUIGG

Attesting Officer      Commissioner of Patents and Trademarks

UNITED STATES PATENT AND TRADEMARK OFFICE

CERTIFICATE EXTENDING PATENT TERM
UNDER 35 U.S.C. 156

Patent No.   : 4,374,829

Dated        : February 22, 1983

Inventor(s)  : Elbert E. Harris et al

Patent Owner : Merck & Co., Inc.

This is to certify that there has been presented to the

COMMISSIONER OF PATENTS AND TRADEMARKS an application under 35 U.S.C. 156 for an extension of the patent term. Since it appears that the requirements of law have been met, this certificate extends the term of the patent for the period of

676 DAYS with all rights pertaining thereto as provided by 35 USC 156(b).

I have caused the seal of the Patent and Trademark Office to be affixed this Twenty-Eighth day of December 1988.

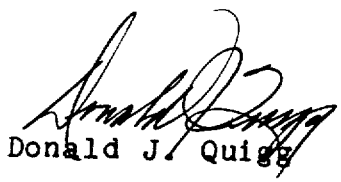

Donald J. Quigg

Assistant Secretary and Commissioner of Patents and Trademarks